(12) United States Patent
Hayashi et al.

(10) Patent No.: US 8,194,241 B2
(45) Date of Patent: Jun. 5, 2012

(54) APPARATUS AND METHOD FOR INSPECTING EDGE OF SEMICONDUCTOR WAFER

(75) Inventors: Yoshinori Hayashi, Yokohama (JP); Hideki Mori, Yokohama (JP)

(73) Assignee: Shibaura Mechatronics Corporation, Yokohama-shi (JP)

(*) Notice: Subject to any disclaimer, the term of this patent is extended or adjusted under 35 U.S.C. 154(b) by 238 days.

(21) Appl. No.: 12/531,429

(22) PCT Filed: Mar. 28, 2008

(86) PCT No.: PCT/JP2008/056209
§ 371 (c)(1),
(2), (4) Date: Sep. 15, 2009

(87) PCT Pub. No.: WO2008/123459
PCT Pub. Date: Oct. 16, 2008

(65) Prior Publication Data
US 2010/0026997 A1 Feb. 4, 2010

(30) Foreign Application Priority Data
Mar. 30, 2007 (JP) ................... 2007-091343

(51) Int. Cl.
*G01N 21/00* (2006.01)
(52) U.S. Cl. ............... 356/237.1; 356/237.2; 356/237.5
(58) Field of Classification Search ..... 356/237.1–237.5
See application file for complete search history.

(56) References Cited

U.S. PATENT DOCUMENTS 7,280,197 B1 * 10/2007 Rosengaus ............... 356/237.1
7,403,278 B2 * 7/2008 Hayashi et al. ........... 356/237.1
2007/0222977 A1   9/2007 Hayashi et al. ........... 356/237.2

FOREIGN PATENT DOCUMENTS

DE   698 00 756   5/2000
(Continued)

OTHER PUBLICATIONS

International Search Report for International Application No. PCT/JP2008/056209 dated Jul. 2, 2008.
German Office Action issued in counterpart application No. 11 2008 000 723.3-33 mailed Nov. 23, 2011 with partial English translation (5 pages).

(Continued)

*Primary Examiner* — Michael P Stafira
(74) *Attorney, Agent, or Firm* — Kratz, Quintos & Hanson, LLP

(57) ABSTRACT

A linear actuator which can make a bed flat in emergency. A linear actuator (10) comprising a shaft (16) having an externally threaded portion (17), a worm reduction gear for transmitting rotation of a motor (40) to the shaft (16), a nut (19) screwing on the externally threaded portion (17) and advancing or retreating as the shaft (16) rotates forward or reversely, and a moving tube (12) secured to the nut (19) and advancing or retreating for the housing (11) is further provided with a sub-shaft (52) interlocked with the worm reduction gear, an inner race (59) spline coupled with the sub-shaft (52), an engaging male portion (82) and an engaging female portion (83) interposed between the inner race (59) and the collar (55) of the shaft (16) to engage freely with each other, an operating ring (66) fitted rotatably to the outer circumference of the housing (11), and a working ring (72) for transmitting the rotation of the operating ring (66) to the inner race (59) while converting into axial movement. The shaft (16) can be rotated freely in emergency by disengaging the engaging male portion and the engaging female portion.

10 Claims, 24 Drawing Sheets

FOREIGN PATENT DOCUMENTS

| | | |
|---|---|---|
| EP | 1 001 460 | 5/2001 |
| JP | 2001-4341 A1 | 1/2001 |
| JP | 2003-243465 A1 | 8/2003 |
| JP | 3709426 | 8/2005 |
| WO | WO 2006/059647 | 6/2006 |
| WO | WO 2006/059647 A1 | 6/2006 |

OTHER PUBLICATIONS

"Wafer Geometry Inspector WGI 300 mit ARDAS-LS Lichtschnitttechnik"; KoCoS Optical Measurement GmbH with English translation (15 pages).

* cited by examiner

[FIG.1A]
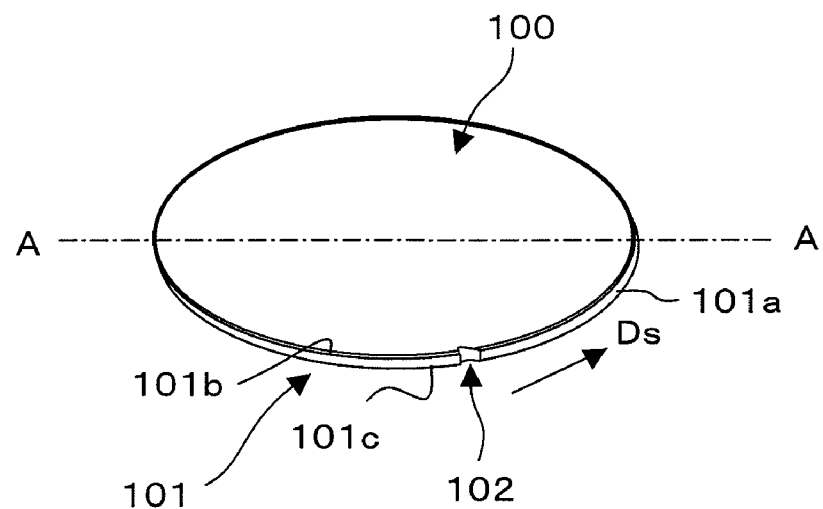
[FIG.1B]
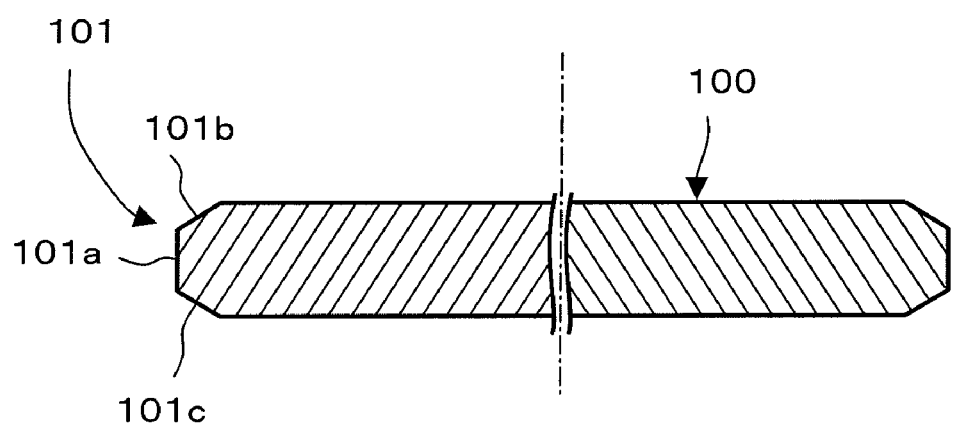

[FIG.2]
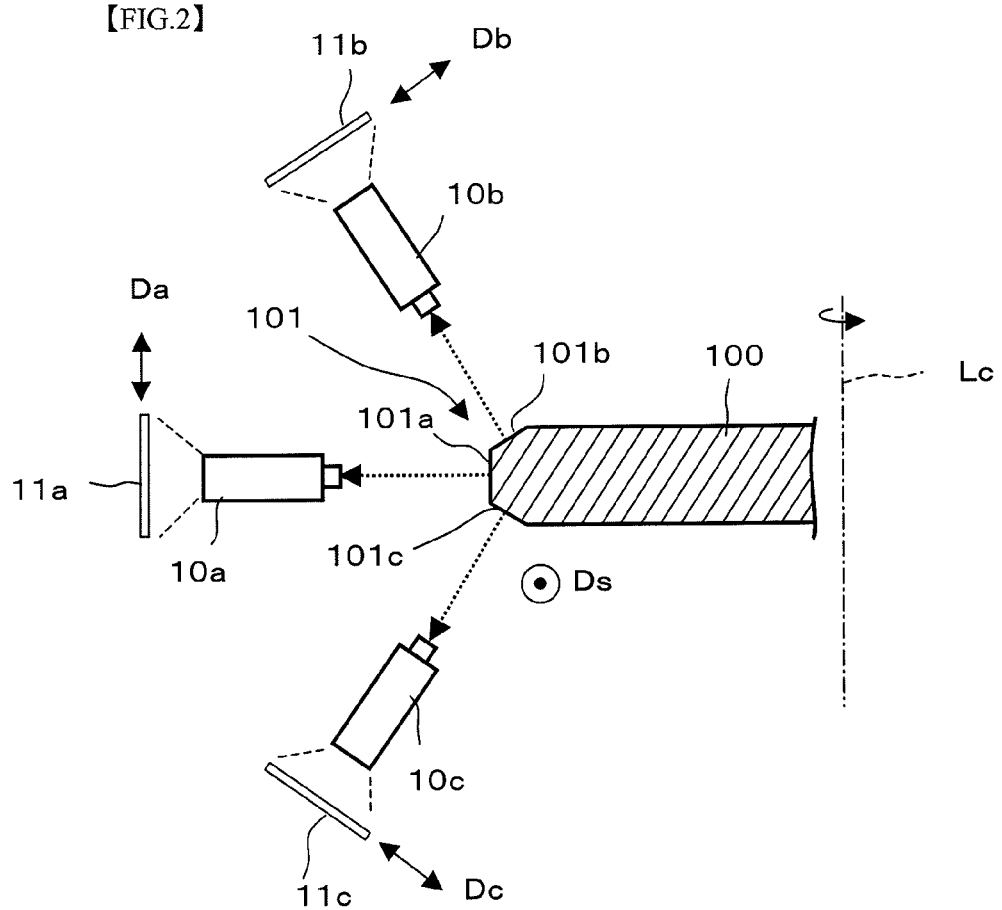
[FIG.3]
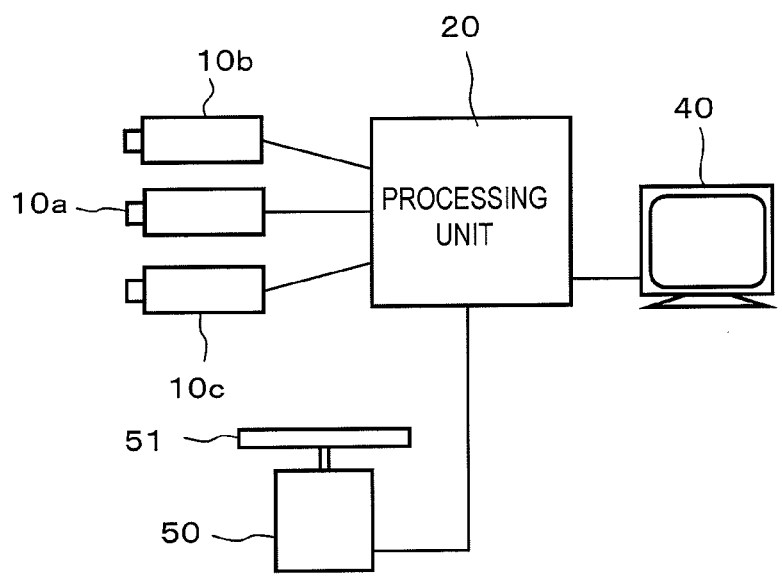

[FIG.4]
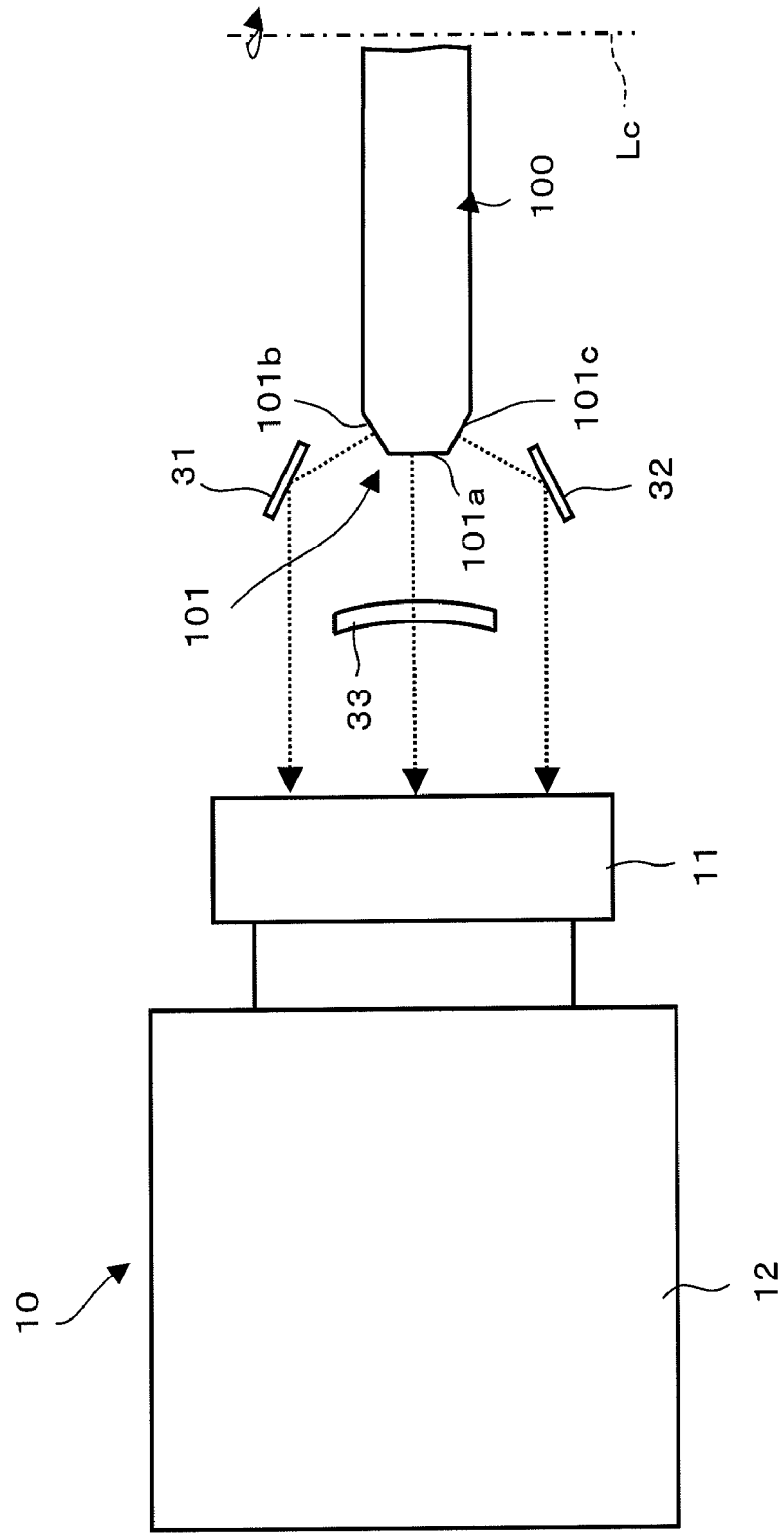

[FIG.5]
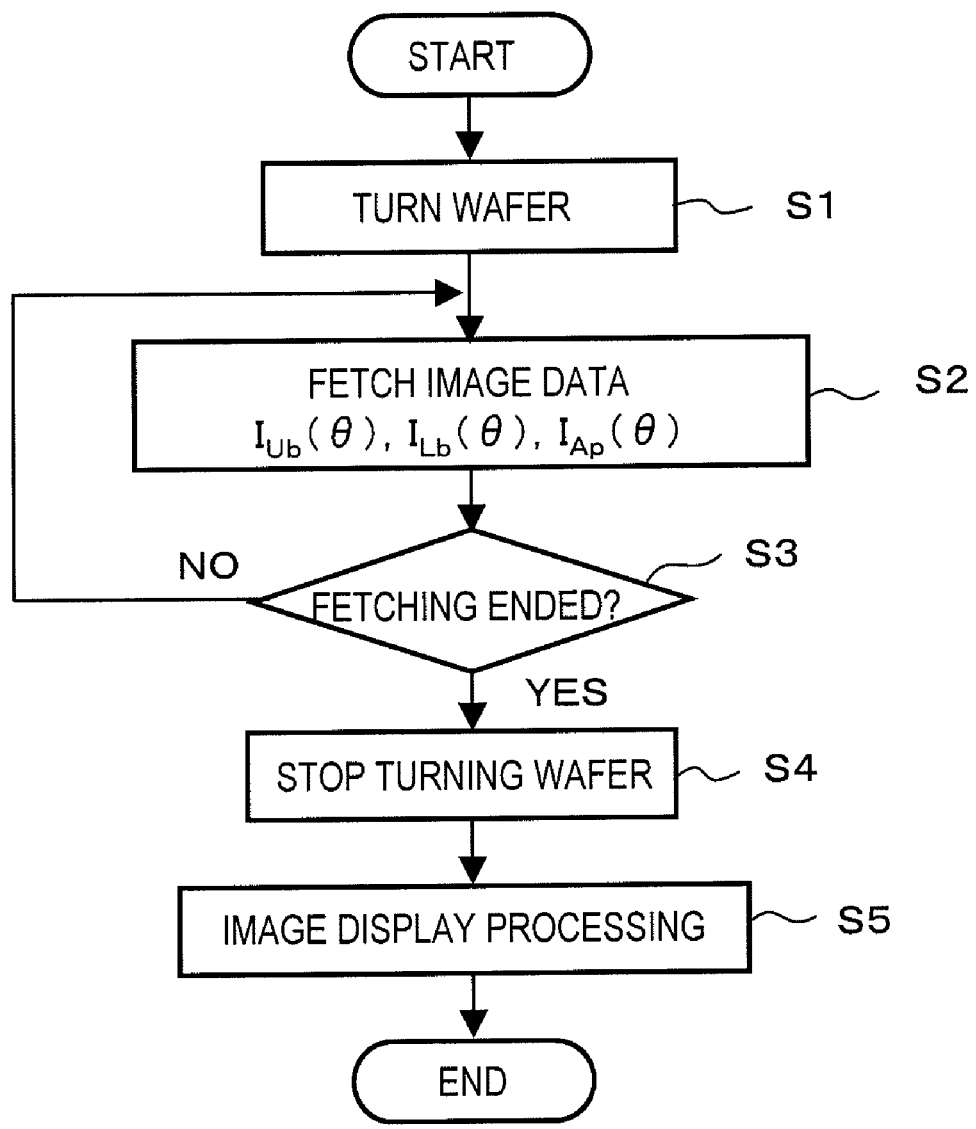

[FIG.6]
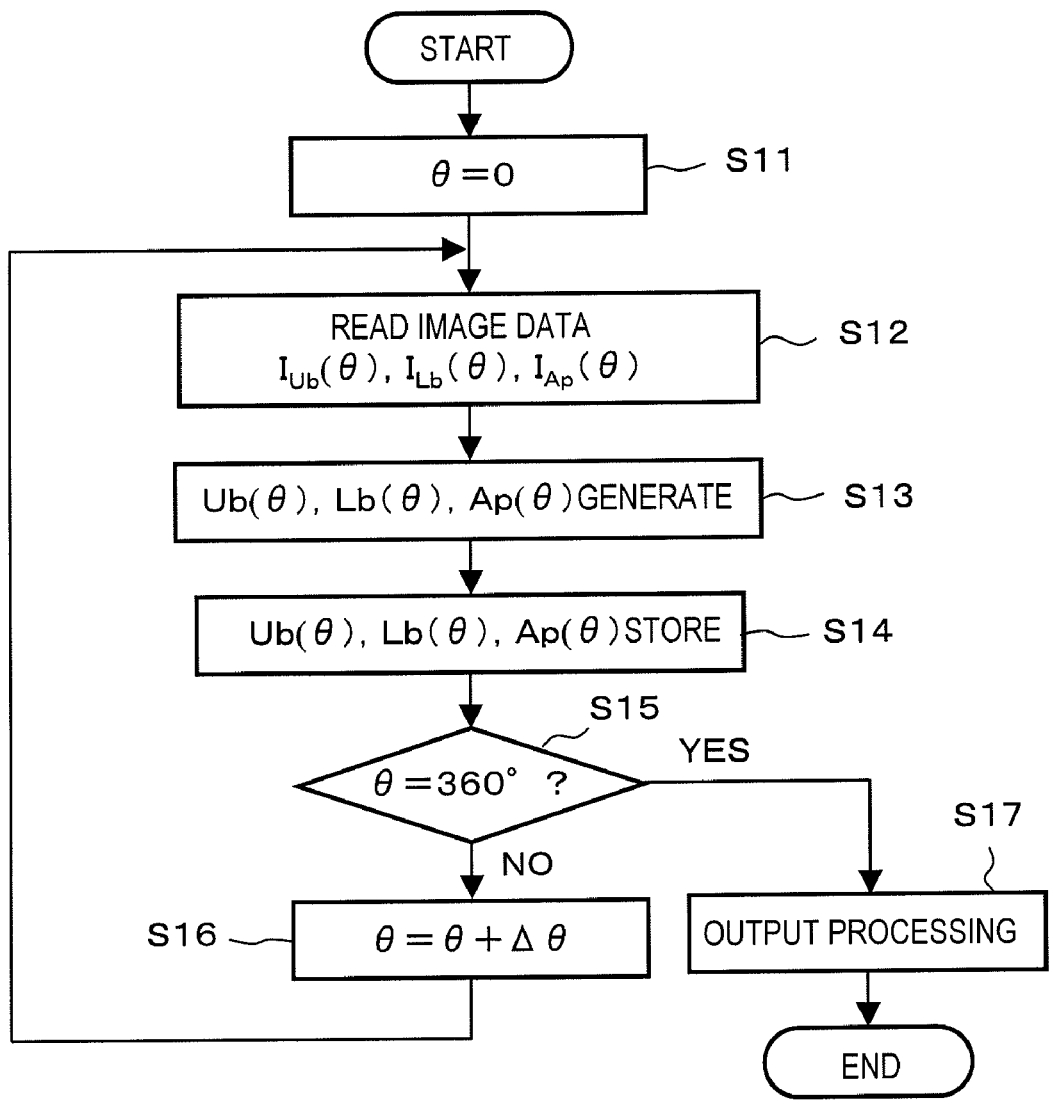

[FIG.7]
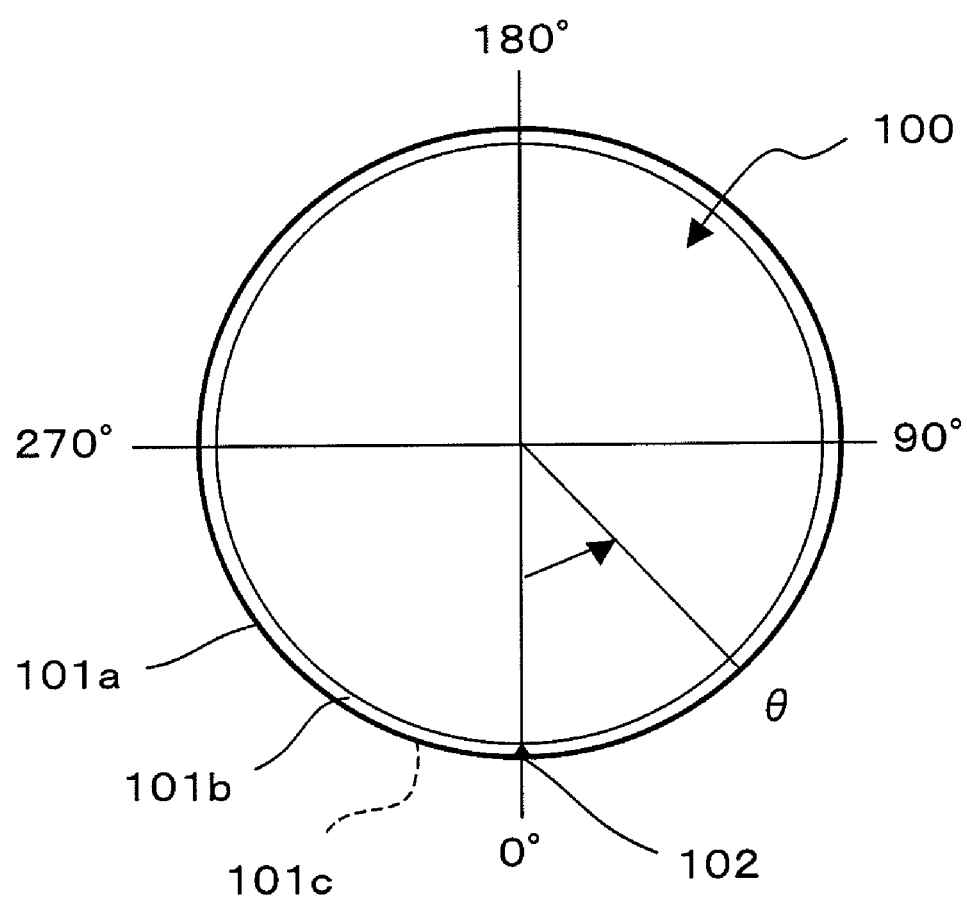

[FIG.8]
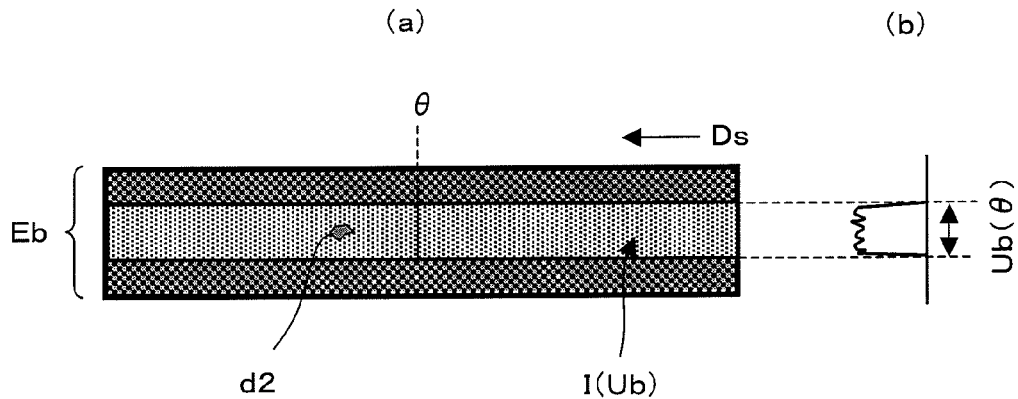
[FIG.9]
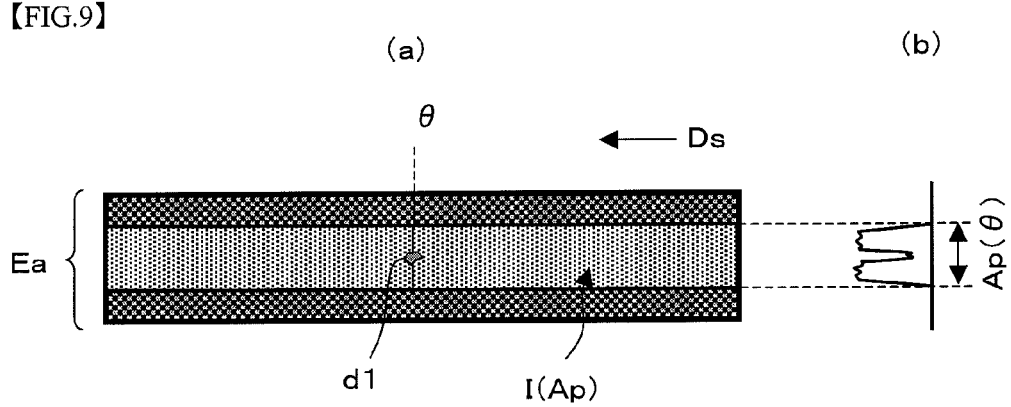
[FIG.10]
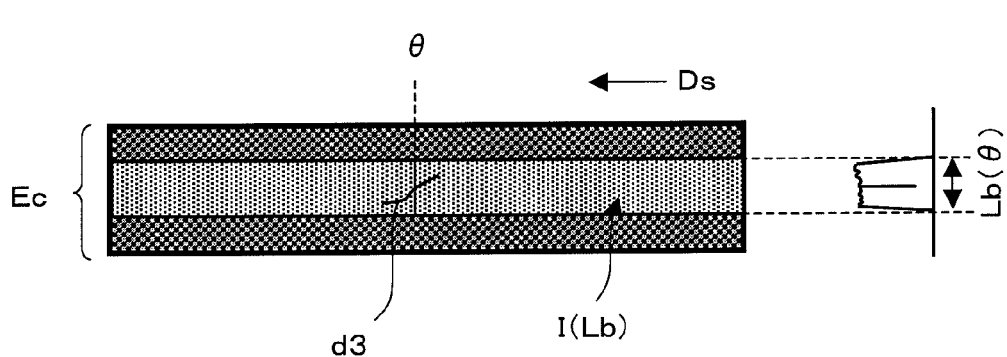

[FIG.11]
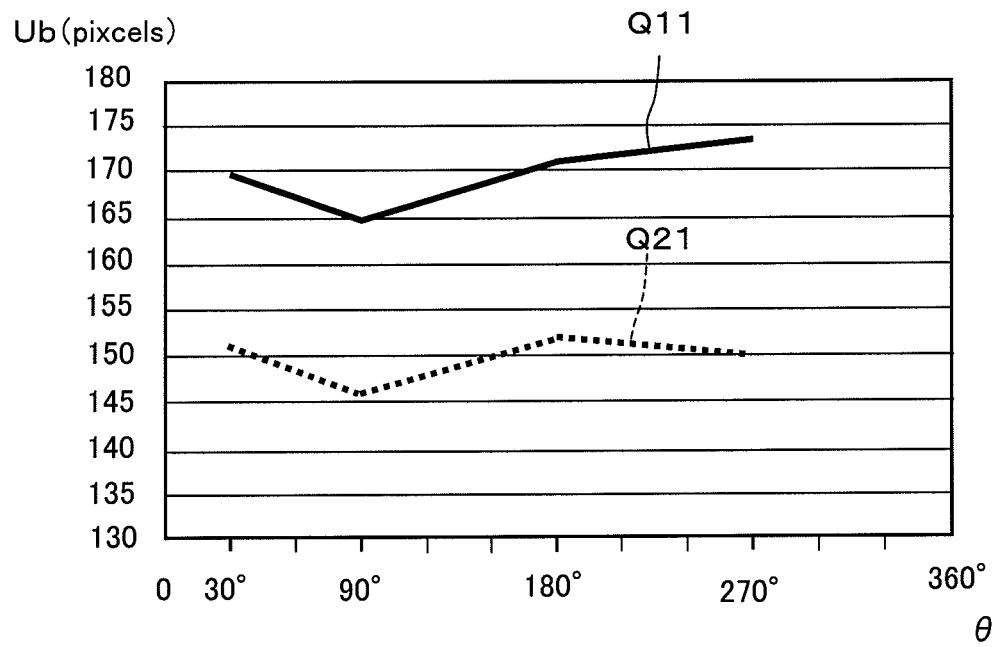
[FIG.12]
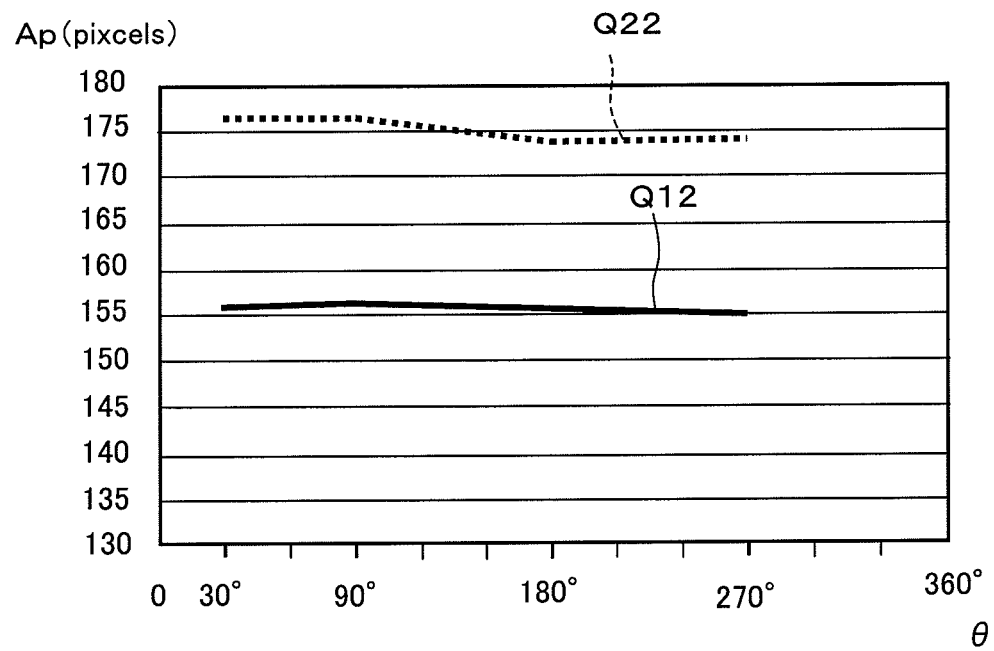

[FIG.13]
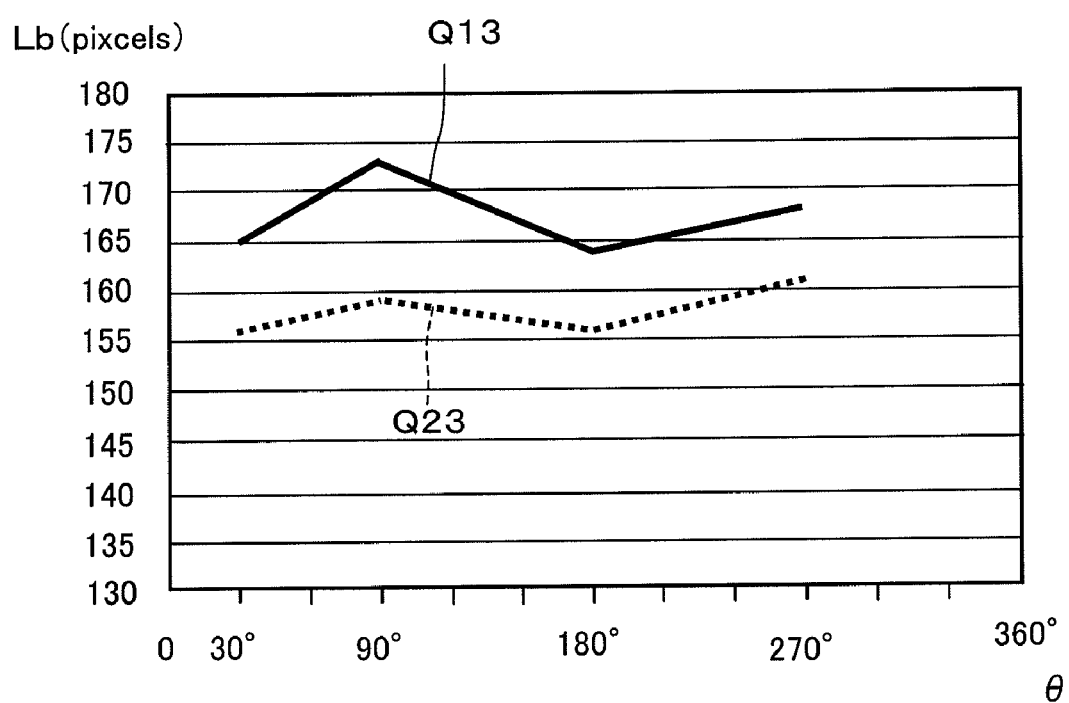

[FIG.14A]
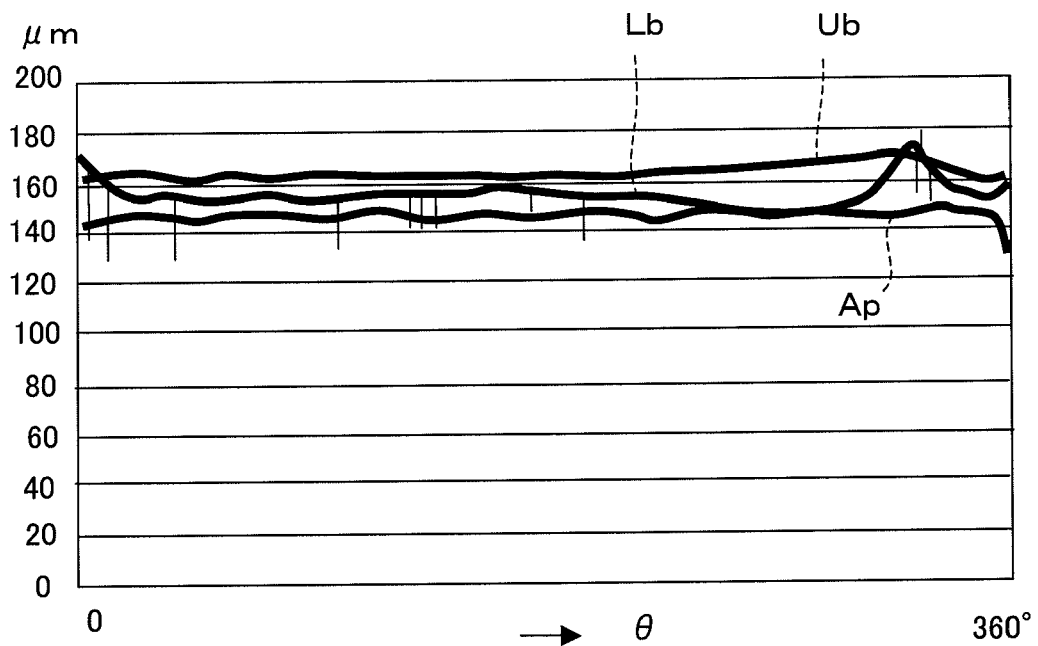
MEASUREMENT VALUES OF Ap, Ub, AND Lb
[FIG.14B]
|     | MAX    | MIN    | AVE    | STD   |
|-----|--------|--------|--------|-------|
| Ub  | 547.20 | 499.20 | 524.77 | 7.45  |
| Ap  | 483.20 | 412.80 | 470.52 | 4.63  |
| Lb  | 569.60 | 412.80 | 495.34 | 14.90 |

[FIG.15A]
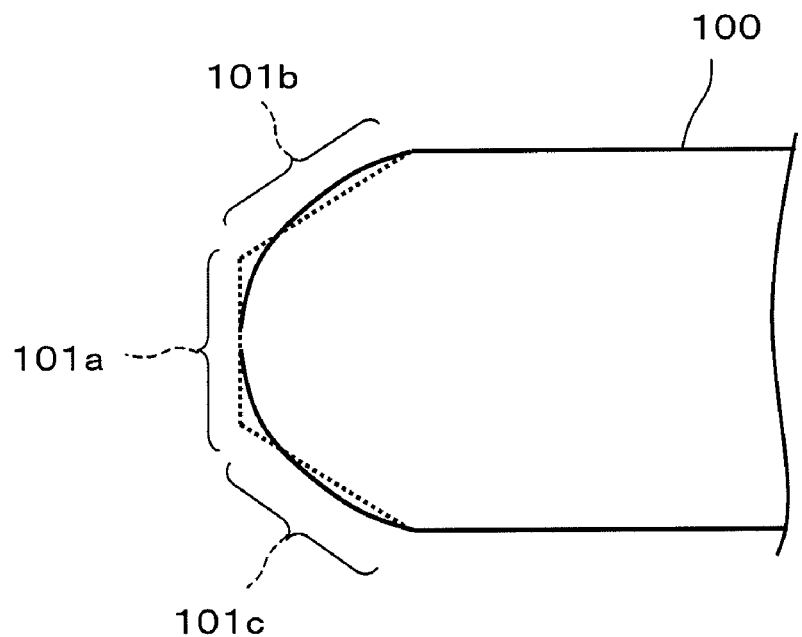
[FIG.15B]
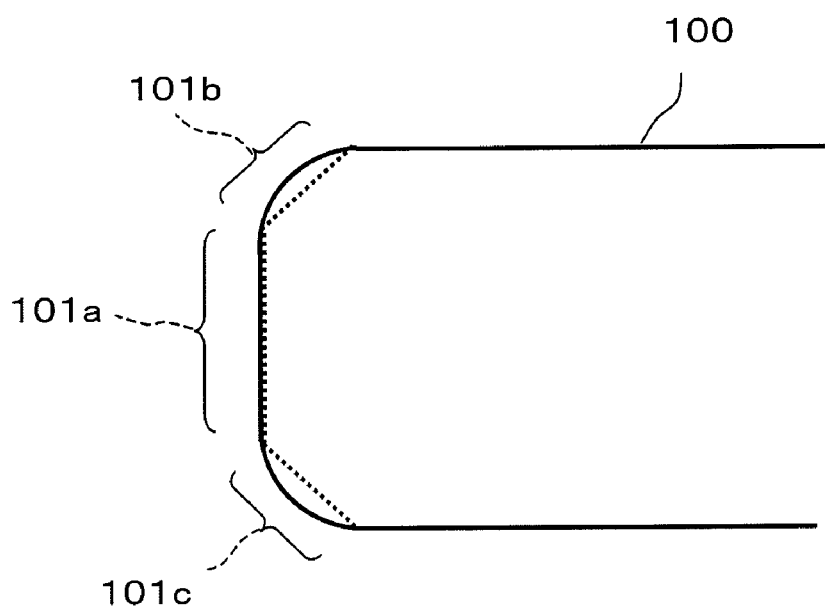

[FIG.16]
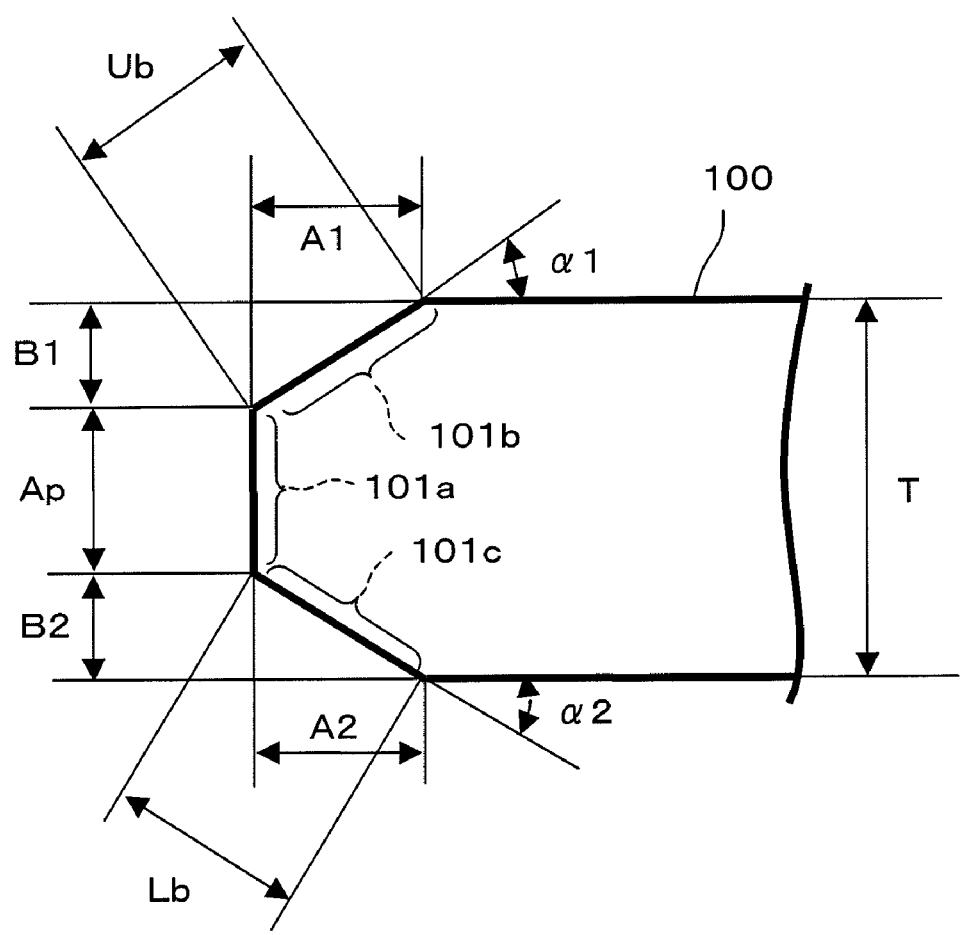

【FIG.17】
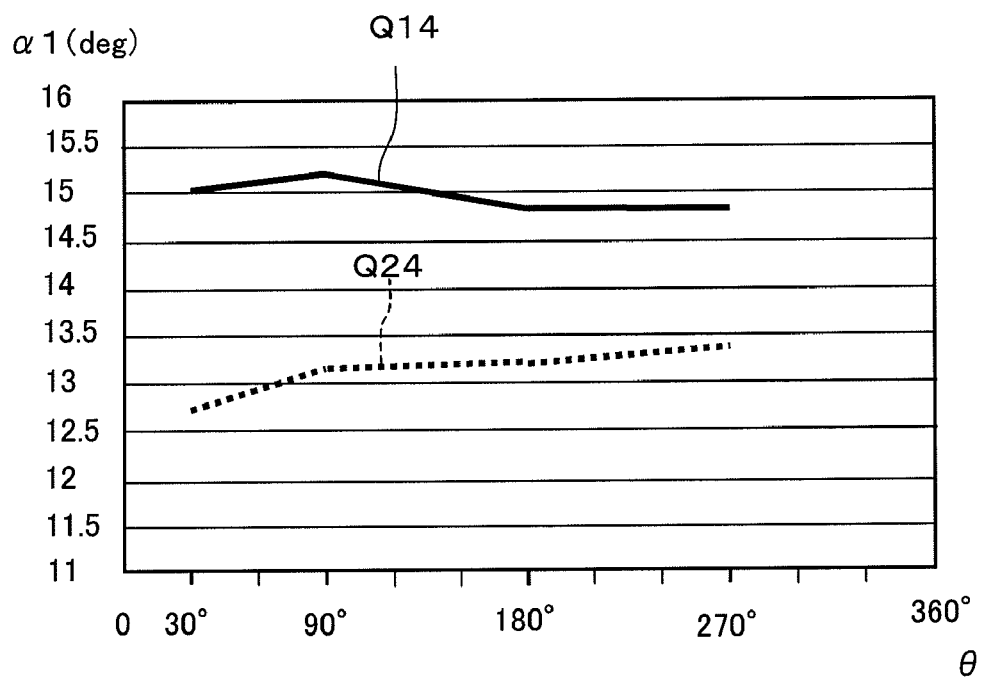
【FIG.18】
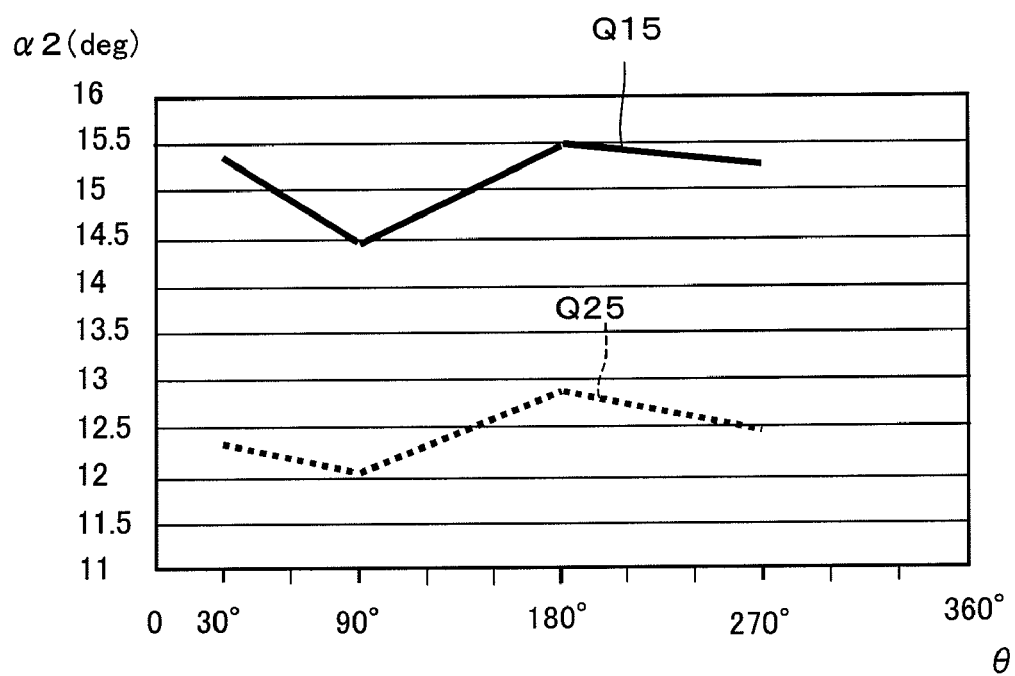

[FIG.19]
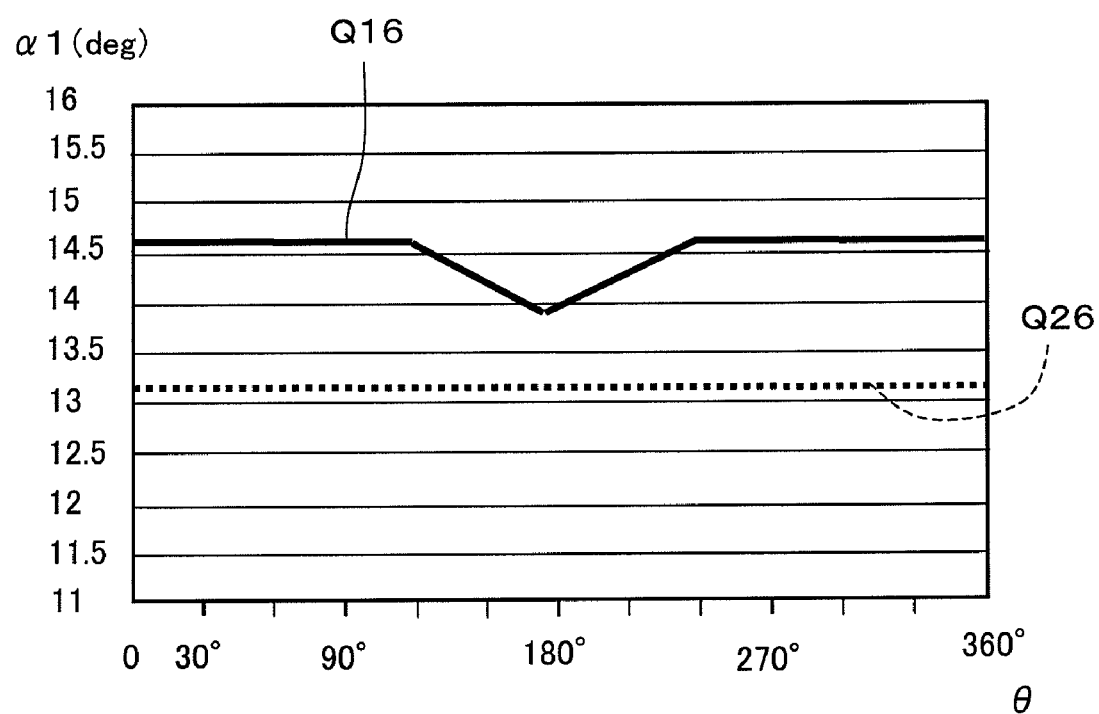

[FIG.20]
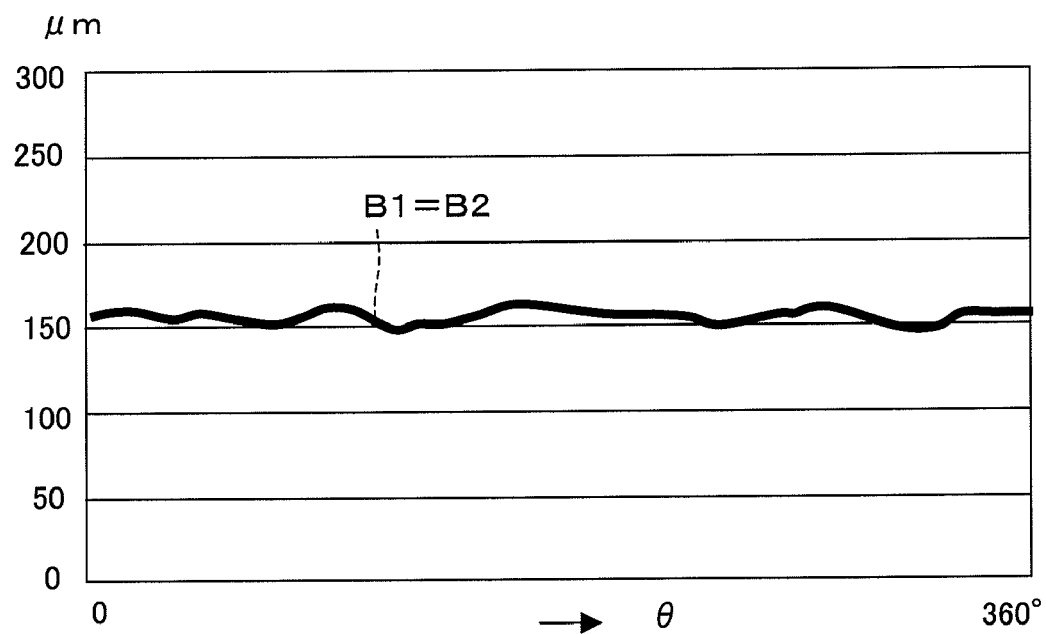

【FIG.21A】
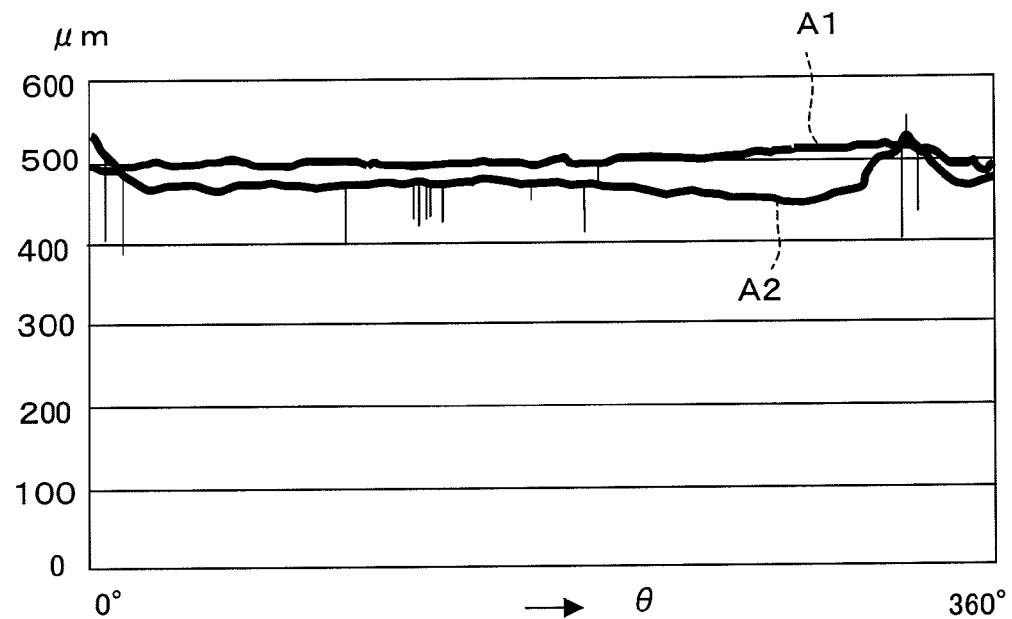
FIRST APPROXIMATION VALUES OF A1 AND A2
【FIG.21B】
|    | MAX    | MIN    | AVE    | STD   |
|----|--------|--------|--------|-------|
| A1 | 525.40 | 475.20 | 501.99 | 7.79  |
| A2 | 548.69 | 393.44 | 471.13 | 15.64 |

[FIG.22A]
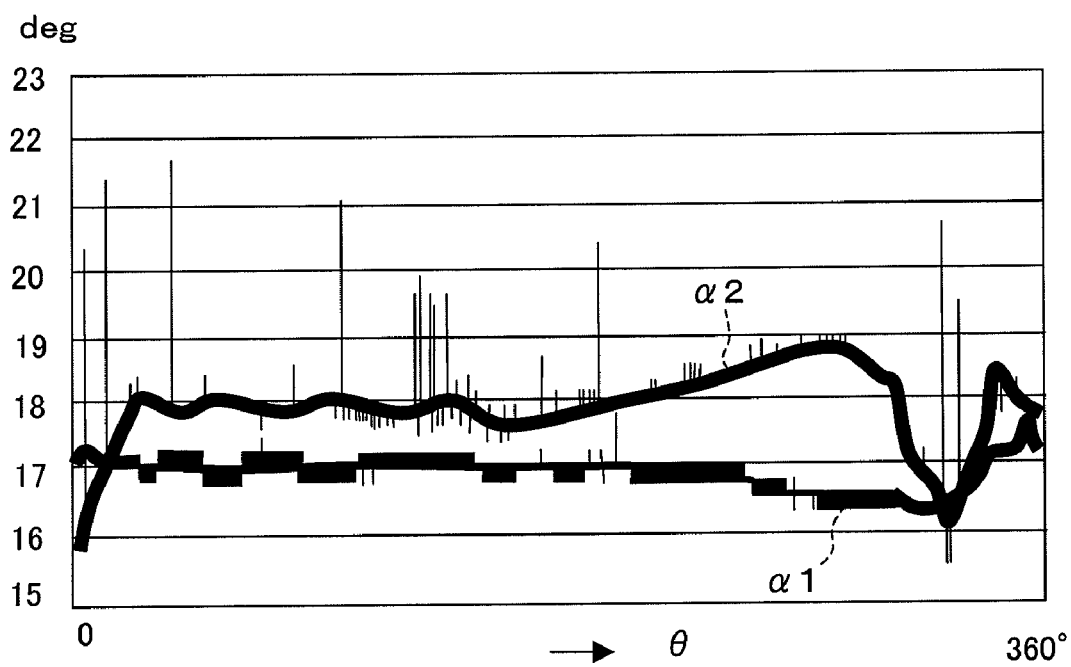
[FIG.22B]
|   | MAX | MIN | AVE | STD |
|---|---|---|---|---|
| $\alpha 1$ | 17.84 | 16.23 | 16.94 | 0.25 |
| $\alpha 2$ | 21.74 | 15.57 | 18.00 | 0.54 |

[FIG.23]
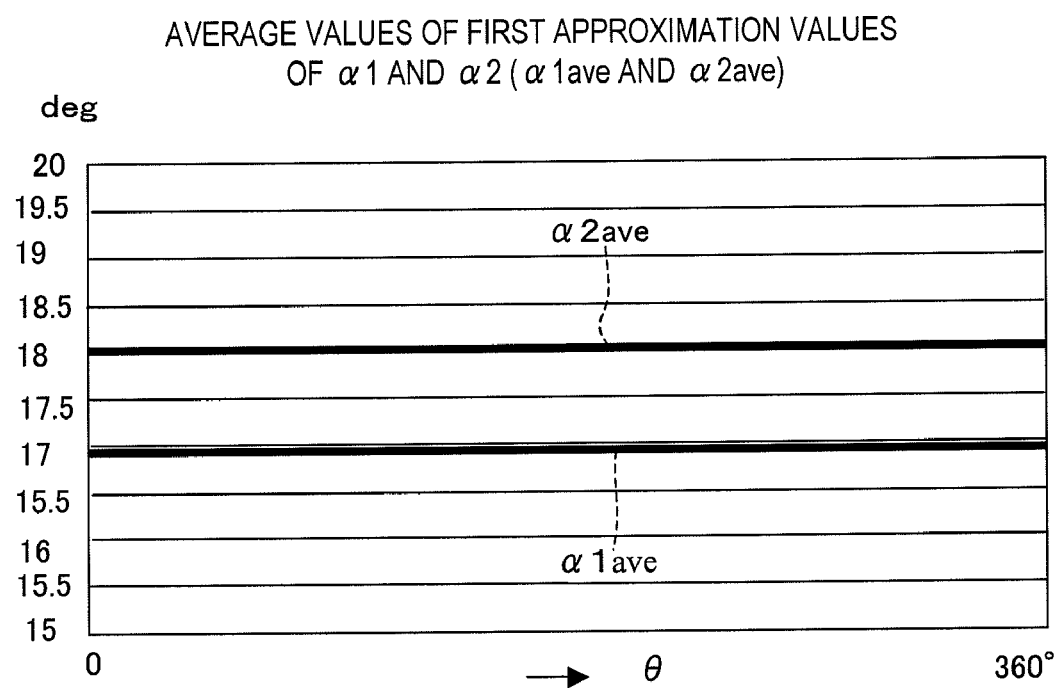

[FIG.24A]
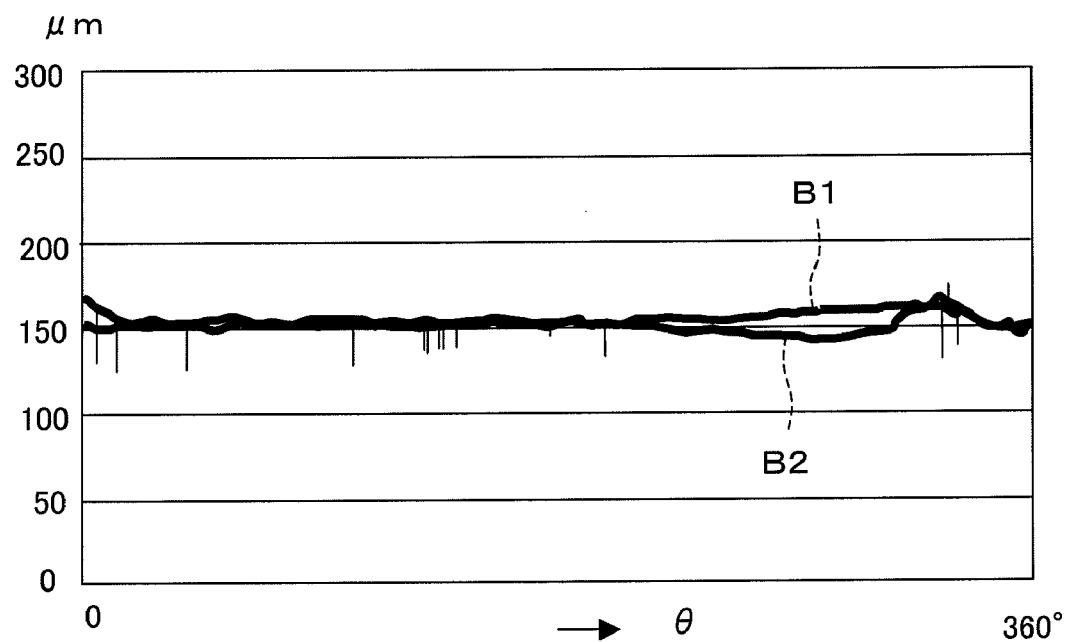
FIRST APPROXIMATION VALUES OF B1 AND B2
[FIG.24B]
|    | MAX    | MIN    | AVE    | STD  |
|----|--------|--------|--------|------|
| B1 | 161.71 | 147.52 | 155.08 | 2.20 |
| B2 | 173.76 | 125.93 | 151.11 | 4.55 |

[FIG.25A]
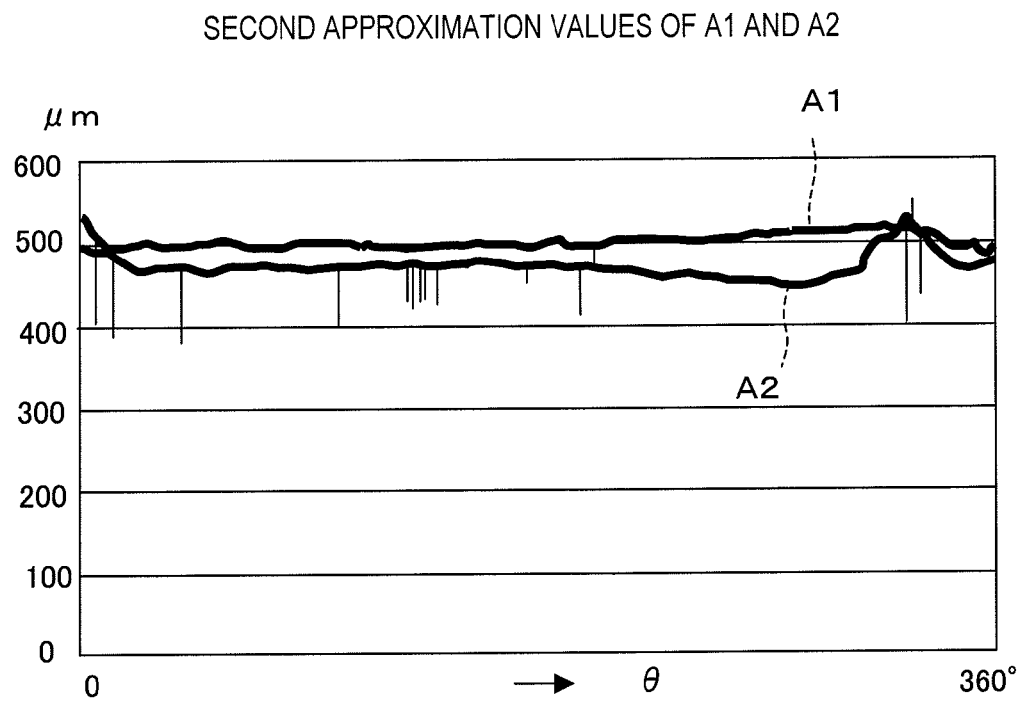
[FIG.25B]
|  | MAX | MIN | AVE | STD |
|---|---|---|---|---|
| A1 | 522.76 | 476.90 | 501.33 | 7.12 |
| A2 | 542.45 | 393.12 | 471.73 | 14.19 |

[FIG.26]
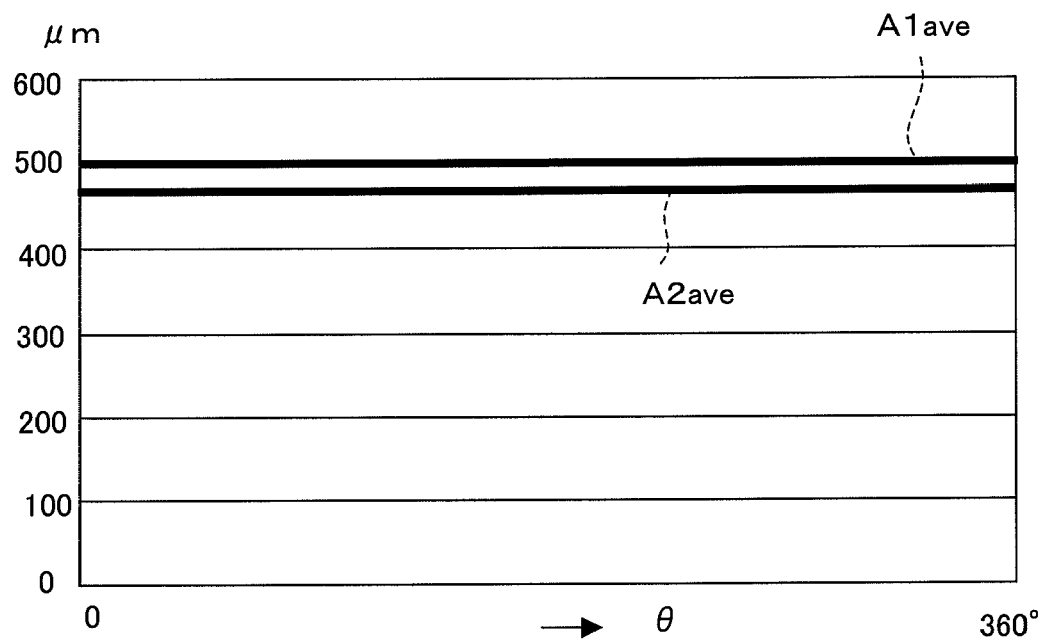

【FIG.27A】
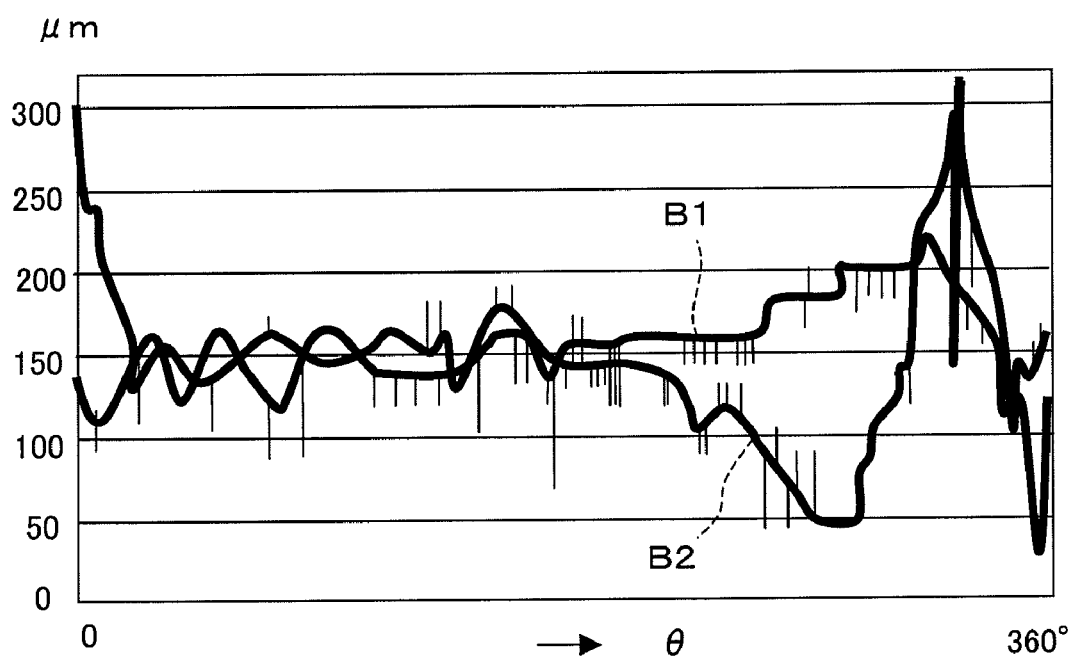
SECOND APPROXIMATION VALUES OF B1 AND B2
【FIG.27B】
|    | MAX    | MIN   | AVE    | STD   |
|----|--------|-------|--------|-------|
| B1 | 219.31 | 32.77 | 153.20 | 25.37 |
| B2 | 319.24 | 42.07 | 145.31 | 46.90 |

[FIG.28A]
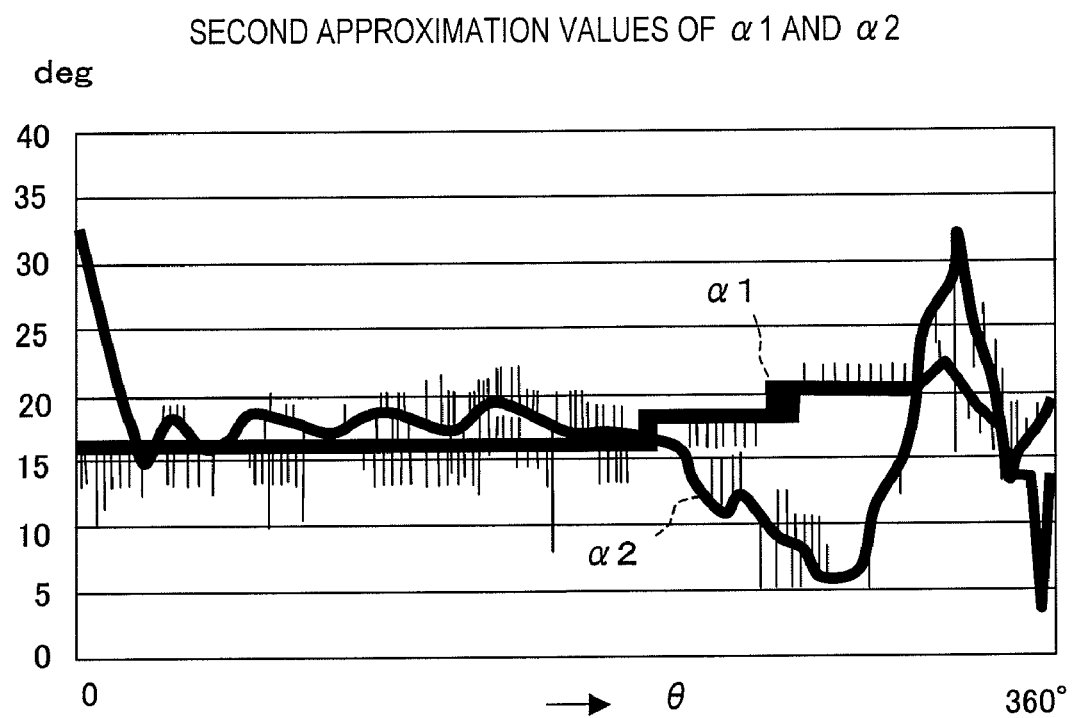
SECOND APPROXIMATION VALUES OF $\alpha 1$ AND $\alpha 2$
[FIG.28B]
|  | MAX | MIN | AVE | STD |
|---|---|---|---|---|
| $\alpha 1$ | 23.63 | 3.74 | 16.96 | 2.65 |
| $\alpha 2$ | 34.09 | 5.09 | 16.98 | 5.13 |

【FIG.29A】
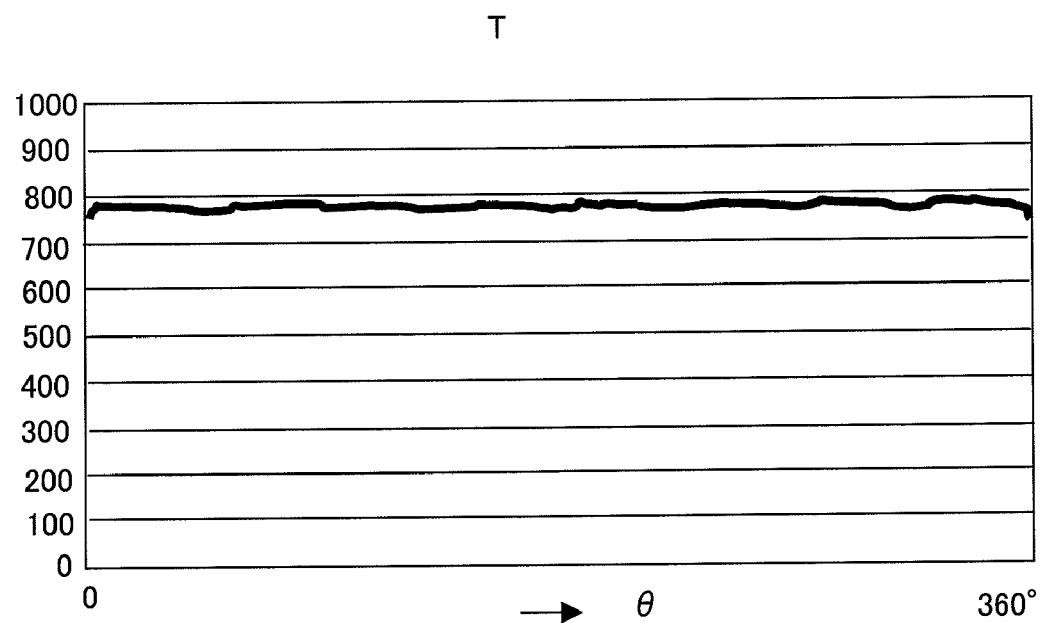
【FIG.29B】
|   | MAX | MIN | AVE | STD |
|---|---|---|---|---|
| T | 789.02 | 718.62 | 776.33 | 4.63 |

APPARATUS AND METHOD FOR INSPECTING EDGE OF SEMICONDUCTOR WAFER

TECHNICAL FIELD

The present invention relates to an edge inspection apparatus and edge inspection method of a semiconductor wafer inspecting an outer circumference edge part of a semiconductor wafer.

BACKGROUND ART

In the past, a measurement apparatus (inspection apparatus) for measuring a cross-sectional shape of an outer circumference edge part of a semiconductor wafer has been proposed (see Patent Literature 1). This measurement apparatus projects light to the outer circumference edge part of a semiconductor wafer parallel to the surface of the semiconductor wafer and in its tangential direction, has the light passing the outer circumference edge part and proceeding via an optical system forming a telecentric structure received by an image sensor, and thereby forms a cross-sectional projection of the outer circumference edge part on the image sensor. Further, two-dimensional dimensions of the outer circumference edge part of the semiconductor wafer are measured from the image corresponding to the cross-sectional projection of the outer circumference edge part of the semiconductor wafer obtained based on the signal output from the image sensor.

According to such a measurement apparatus, the two-dimensional dimensions of the outer circumference edge part of the semiconductor wafer can be measured, so it is possible to inspect the suitability of the shape of the outer circumference edge part of the semiconductor wafer based on the measurement results.

In this regard, the outer circumference edge part of a semiconductor wafer is preferably inspected not only for the shape, but also for the presence of cracks, particles, or other defects at the outer circumference edge part. In the past, an inspection apparatus performing that type of inspection has been proposed (see Patent Literature 2). This inspection apparatus has a line sensor capturing an outer circumference end face of the outer circumference edge part of the semiconductor wafer, a line sensor capturing a slanted surface at an outer circumference rim of one surface of the semiconductor wafer, and a line sensor capturing a slanted surface at an outer circumference rim of the other surface of the semiconductor wafer. Further, using the shading distribution, color distribution, or other state of the outer circumference edge part of the semiconductor wafer obtained based on the signals detected from the line sensor, the presence of cracks, particles, or other defects at the outer circumference end face or slanted surfaces of the outer circumference edge part of the semiconductor wafer is judged.

According to this inspection apparatus, even the presence of defects of the outer circumference edge part of the semiconductor wafer which cannot be found by visual inspection can be precisely inspected.

Patent Literature 1: Japanese Patent Publication (A) No. 2006-145487
Patent Literature 2: Japanese Patent Publication (A) No. 2003-243465

SUMMARY OF INVENTION

Technical Problem

The inspection apparatus for inspecting the shape of an outer circumference edge part of a semiconductor wafer explained above projects light to the outer circumference edge part and measures two-dimensional dimensions from an image expressing its shadow (projection), so it cannot judge cracks, particles, or other defects from that image. For this reason, the inspection apparatus for inspecting the shape of the outer circumference edge part of a semiconductor wafer cannot share components (cameras etc.) or processing with an inspection apparatus for inspecting for cracks, particles, or other defects of that outer circumference edge part. As a result, it is difficult to perform the inspection of the shape of the outer circumference edge part of the semiconductor wafer and the inspection for the presence of cracks, particles, or other defects by the same process (same apparatus).

The present invention was made in consideration of this situation and provides an edge inspection apparatus and edge inspection method of a semiconductor wafer able to easily inspect the shape of an outer circumference edge part of a semiconductor wafer by the same process or same apparatus as the inspection for the presence of cracks, particles, or other defects of the outer circumference edge part.

Solution to Problem

The edge inspection apparatus of a semiconductor wafer according to the present invention is comprised having an imaging unit arranged facing the outer circumference edge part of the semiconductor wafer, successively capturing the outer circumference edge part in a circumferential direction, and outputting an image signal and an image processing unit processing the image signal successfully output from the imaging unit, the image processing unit having an image information generating means for generating image information expressing the outer circumference edge part of the semiconductor wafer from the image signal and a shape information generating means for generating edge shape information expressing shapes of a plurality of positions of the outer circumference edge part from the image information, designed to output inspection results based on the edge shape information.

Due to this configuration, image information expressing the outer circumference edge part of the semiconductor wafer is generated from an image signal from an imaging unit able to change in accordance with the state of cracks, particles, or other defects at the outer circumference edge part of the semiconductor wafer, so that image information can express the outer circumference edge part including the defects etc. Further, edge shape information expressing the shape of each of a plurality of positions of the outer circumference edge part is generated from that type of image information and inspection results based on that edge shape information are output.

The number of positions for generating the edge shape information of the outer circumference edge part of the semiconductor wafer is preferably as large as possible. By generating the edge shape information at more positions across the entire circumference of the outer circumference edge part of the semiconductor wafer, it becomes possible to more accurately evaluate the shape across the entire circumference of the outer circumference edge part from the inspection results based on that edge shape information.

The inspection results may be edge shape information corresponding to each position at the outer circumference edge part of the semiconductor wafer output in a predetermined format or may be some sort of evaluation information obtained from edge shape information of a plurality of positions of the outer circumference edge part.

Further, in the edge inspection apparatus of a semiconductor wafer according to the present invention, the apparatus may be configured so that the imaging unit captures at least one of an outer circumference end face of the semiconductor wafer, a first outer circumference bevel surface slanted at an outer circumference rim of a first surface of the semiconductor wafer, and a second outer circumference bevel surface slanted at an outer circumference rim of a second surface at an opposite side from the first surface as the outer circumference edge part of the semiconductor wafer, and the shape information generating means generates at least one of information expressing the shape at each of a plurality of positions of the outer circumference end face from image information expressing an outer circumference end face of the semiconductor wafer, information expressing the shape at each of a plurality of positions of the first outer circumference bevel surface from image information expressing a first outer circumference bevel surface of the semiconductor wafer, and information expressing the shape at each of a plurality of positions of the second outer circumference bevel surface from image information expressing a second outer circumference bevel surface of the semiconductor wafer as the edge shape information.

The outer circumference edge part of a general semiconductor wafer has an outer circumference end face of the semiconductor wafer, a first outer circumference bevel surface slanted at an outer circumference rim of one surface of the semiconductor wafer (first surface), and a second outer circumference bevel surface slanted at an outer circumference rim of another surface of the semiconductor wafer (second surface). In this case, due to the configuration, it becomes possible to accurately evaluate the shapes of the surfaces from the inspection results based on edge shape information expressing the shapes at a plurality of positions of at least one of an outer circumference end face of the semiconductor wafer, first outer circumference bevel surface, and second outer circumference bevel surface.

Furthermore, in the edge inspection apparatus of a semiconductor wafer according to the present invention, the apparatus may be configured so that the shape information generating means generates at least one of outer circumference end face length information expressing a length in a direction cutting across the circumferential direction at each of a plurality of positions of the outer circumference end face from image information expressing the outer circumference end face, first outer circumference bevel surface length information expressing a length in a direction cutting across the circumferential direction at each of a plurality of positions of the first outer circumference bevel surface from image information expressing the first outer circumference bevel surface, and second outer circumference bevel surface length information expressing a length in a direction cutting across the circumferential direction at each of a plurality of positions of the second outer circumference bevel surface from image information expressing the second outer circumference bevel surface as the edge shape information.

Due to this configuration, it becomes possible to accurately perform any of evaluation of a length shape in a direction cutting across the circumferential direction of the outer circumference end face from the inspection results based on the outer circumference end face length information at a plurality of positions of the outer circumference end face of the semiconductor wafer, evaluation of a length shape in a direction cutting across the first outer circumference bevel surface from the inspection results based on first outer circumference bevel surface length information at a plurality of positions of the first outer circumference bevel surface of the semiconductor wafer, and evaluation of a length shape in a direction cutting across the second outer circumference bevel surface from the inspection results based on second outer circumferential bevel surface length information at a plurality of positions of the second outer circumference bevel surface of the semiconductor wafer.

Further, in the edge inspection apparatus of a semiconductor wafer according to the present invention, the apparatus may be configured so that the shape information generating means generates outer circumference end face length information expressing a length in a direction cutting across the circumferential direction at each of a plurality of positions of the outer circumference end face from image information expressing the outer circumference end face, first outer circumference bevel surface length information expressing a length in a direction cutting across the circumferential direction at each of a plurality of positions of the first outer circumference bevel surface from image information expressing the first outer circumference bevel surface, and second outer circumference bevel surface length information expressing a length in a direction cutting across the circumferential directions at each of a plurality of positions of the second outer circumference bevel surface from image information expressing the second outer circumference bevel surface and, based on the outer circumference surface length information, the first outer circumference bevel surface length information, and the second outer circumference bevel surface length information, generates at least one of first outer circumference bevel surface angle information expressing a slant angle at each of said plurality of positions of the first outer circumference bevel surface, second outer circumference bevel surface angle information expressing a slant angle at each of said plurality of positions of the second outer circumference bevel surface, first outer circumference bevel surface diametrical direction component length information expressing a length component in a diametrical direction of the semiconductor wafer at each of the plurality of positions of the first outer circumference bevel surface, second outer circumference bevel surface diametrical direction component length information expressing a length component in the diametrical direction at each of the plurality of positions of the second outer circumference bevel surface, first outer circumference bevel surface axial direction component length information expressing a length component in an axial direction vertical to the semiconductor wafer at each of the plurality of positions of the first outer circumference bevel surface, and second outer circumference bevel surface axial direction component length information expressing a length component in the axial direction at each of the plurality of positions of the second outer circumference bevel surface as the edge shape information.

Due to this configuration, it becomes possible to accurately evaluate a shape relating to a slant angle of the first outer circumference bevel surface from inspection results based on first outer circumference bevel surface angle information at a plurality of positions of a first outer circumference bevel surface of the semiconductor wafer, evaluate a shape relating to a slant angle of the second outer circumference bevel surface from inspection results based on second outer circumference bevel surface angle information at a plurality of positions of a second outer circumference bevel surface of the semiconductor wafer, and evaluate a shape relating to a length component in a diametrical direction of the semiconductor wafer of the first outer circumference bevel surface from inspection results based on first outer circumference bevel surface diametrical direction component length information at a plurality of positions of the first outer circumference bevel surface, a shape relating to a length component in a diametrical direction of the semiconductor wafer of the second outer circumference bevel surface from inspection results based on second outer circumference bevel surface diametrical direction component length information at a plurality of positions of the second outer circumference bevel surface, a shape relating to a length component in the axial direction of the first outer circumference bevel surface from inspection results based on first outer circumference bevel surface axial direction length information at a plurality of positions of the first outer circumference bevel surface, and a shape relating to a length component in the axial direction of the second outer circumference bevel surface from inspection results based on second outer circumference bevel surface axial direction length information at a plurality of positions of the second outer circumference bevel surface.

Further, in the edge inspection apparatus of a semiconductor wafer according to the present invention, the apparatus may be configured so that it outputs inspection results based on at least one of a maximum value, minimum value, average value, and standard deviation of a value of edge shape information at each of the plurality of positions based on edge shape information expressing a shape at each of a plurality of positions of the outer circumference edge part.

Further, in the edge inspection apparatus of a semiconductor wafer according to the present invention, the apparatus may be configured so that it outputs inspection results based on at least one of a maximum value, minimum value, average value, and standard deviation of a value of at least one of the outer circumference end face length information, the first outer circumference bevel surface length information, and the second outer circumference bevel surface length information at each of the plurality of positions of the outer circumference edge part.

Furthermore, in the edge inspection apparatus of a semiconductor wafer according to the present invention, the apparatus may be configured so that it outputs inspection results based on at least one of a maximum value, minimum value, average value, and standard deviation of a value of at least one of first outer circumference bevel surface angle information, second outer circumference bevel surface angle information, first outer circumference bevel surface diametrical direction component length information, second outer circumference bevel surface diametrical direction component length information, first outer circumference bevel surface axial direction component length information, and second outer circumference bevel surface axial direction component length information at each of a plurality of positions of the outer circumference edge part.

Due to the above-mentioned configuration, it becomes possible to use inspection results of at least one of the maximum value, minimum value, average value, and standard deviation of a value of edge shape information at a plurality of positions of the outer circumference edge part of the semiconductor wafer so as to easily manage the trends in shape of that outer circumference edge part in the process of production of a semiconductor wafer 100.

The edge inspection method of a semiconductor wafer according to the present invention has an edge capturing step using an imaging unit arranged facing an outer circumference edge part of a semiconductor wafer to capture an outer circumference edge part and an image processing step processing an image signal capturing the outer circumference edge part of the semiconductor wafer successively output from the imaging unit, the image processing step having an image information generating step generating image information expressing the outer circumference edge part of the semiconductor wafer from the image signal and a shape information generating step generating edge shape information expressing an edge shape at each of a plurality of positions of the outer circumference edge part from the image information, so as to obtain inspection results based on the edge shape information.

Further, in the edge inspection method of a semiconductor wafer as set forth in the present invention, the method may be configured so that the edge capturing step uses the imaging unit to capture at least one of an outer circumference end face of the semiconductor wafer, a first outer circumference bevel surface slanted at an outer circumference rim of a first surface of the semiconductor wafer, and a second outer circumference bevel surface slanted at an outer circumference rim of a second surface at an opposite side from the first surface as the outer circumference edge part of the semiconductor wafer, and the shape information generating step generates at least one of information expressing a shape at each of a plurality of positions of the outer circumference end face from image information expressing an outer circumference end face of the semiconductor wafer, information expressing a shape at each of a plurality of positions of the first outer circumference bevel surface from image expressing a first outer circumference bevel surface of the semiconductor wafer, and information expressing a shape at each of a plurality of positions of the second outer circumference bevel surface from image information expressing a second outer circumference bevel surface of the semiconductor wafer as the edge shape information.

Furthermore, in the edge inspection method of a semiconductor wafer according to the present invention, the method may be configured so that the shape information generating step generates at least one of outer circumference end face length information expressing a length of a direction cutting across the circumferential direction at each of a plurality of positions of the outer circumference end face from image information expressing the outer circumference end face, first outer circumference bevel surface length information expressing a length in a direction cutting across the circumferential direction at each of a plurality of positions of the first outer circumference bevel surface from image information expressing the first outer circumference bevel surface, and second outer circumference bevel surface length information expressing a length in a direction cutting across the circumferential direction at each of a plurality of positions of the second outer circumference bevel surface from image information expressing the second outer circumference bevel surface as the edge shape information.

Advantageous Effects of the Invention

According to the edge shape inspection apparatus and edge inspection method according to the present invention, image information generated from an image signal output from an imaging unit capturing an outer circumference edge part of a semiconductor wafer can express cracks, particles, or other defects of the outer circumference edge part. Edge shape information expressing the shape of the outer circumference edge part is generated from that type of image information, so it becomes possible to easily inspect the shape of an outer circumference edge part of a semiconductor wafer by the same process or same apparatus as inspection for the presence of cracks, particles, or other defects at the outer circumference edge part based on the image information.

BRIEF DESCRIPTION OF DRAWINGS

FIG. 1A A perspective view showing the appearance of a semiconductor wafer to be inspected by an edge inspection apparatus according to an embodiment of the present invention.

FIG. 1B A cross-sectional view along the line A-A of FIG. 1A.

FIG. 2 A view schematically showing main parts of an imaging system of an edge inspection apparatus according to an embodiment of the present invention.

FIG. 3 A block diagram schematically showing main parts of a control system of an edge inspection apparatus according to an embodiment of the present invention.

FIG. 4 A view schematically showing another example of the configuration of an imaging system of an edge inspection apparatus.

FIG. 5 A flowchart showing a processing routine in a processing unit in the control system shown in FIG. 3 (part 1).

FIG. 6 A flowchart showing a processing routine in a processing unit in the control system shown in FIG. 3 (part 2).

FIG. 7 A view for explaining an angular position of a semiconductor wafer.

FIG. 8 A view showing an example of a display image of a first outer circumference bevel surface (a) and a change in shading of that image at an angular position θ (b).

FIG. 9 A view showing an example of a display image of an outer circumference end face (a) and a change in shading of that image at an angular position θ (b).

FIG. 10 A view showing an example of a display image of a second outer circumference bevel surface (a) and a change in shading of that image at an angular position θ (b).

FIG. 11 A view showing an example of output of first outer circumference bevel surface length data Ub(θ) as inspection results.

FIG. 12 A view showing an example of output of outer circumference end face length data Ap(θ) as inspection results.

FIG. 13 A view showing an example of output of second outer circumference bevel surface length data Lb(θ) as inspection results.

FIG. 14A A view showing an example of output of first outer circumference bevel surface length data Ub(θ), outer circumference end face length data Ap(θ), and second outer circumference bevel surface length data Lb(θ) as inspection results.

FIG. 14B A view showing a maximum value (MAX), minimum value (MIN), average value (AVE), and standard deviation (STD) of a first approximation value in the total angular range of each of the first outer circumference bevel surface length data Ub(θ), outer circumference end face length data Ap(θ), and second outer circumference bevel surface length data Lb(θ).

FIG. 15A A view showing an example of the cross-sectional shape of the outer circumference edge part of the semiconductor wafer.

FIG. 15B A view showing another example of the cross-sectional shape of the outer circumference edge part of the semiconductor wafer.

FIG. 16 A view showing an example of edge shape information able to express the shape of an outer circumference edge part.

FIG. 17 A view showing an example of output of first outer circumference bevel surface angle data α1(θ) as inspection results.

FIG. 18 A view showing an example of output of second outer circumference bevel surface angle data α2(θ) as inspection results.

FIG. 19 A view showing another example of output of first outer circumference bevel surface angle data α1(θ) as inspection results.

FIG. 20 A view showing an initial approximation value at each angular position θ of each of B1 (first outer circumference bevel surface axial direction component length data) and B2 (second outer circumference bevel surface axial direction component length data).

FIG. 21A A view showing a first approximation value at each angular position θ of each of A1 (first outer circumference bevel surface diametrical direction component length data) and A2 (second outer circumference bevel surface diametrical direction component length data).

FIG. 21B A view showing a maximum value (MAX), minimum value (MIN), average value (AVE), and standard deviation (STD) of a first approximation value in the total angular range of each of A1 (first outer circumference bevel surface diametrical direction component length data) and A2 (second outer circumference bevel surface diametrical direction component length data).

FIG. 22A A view showing a first approximation value at each angular position θ of each of α1 (first outer circumference bevel surface angle data) and α2 (second outer circumference bevel surface angle data).

FIG. 22B A view showing a maximum value (MAX), minimum value (MIN), average value (AVE), and standard deviation (STD) of a first approximation value at the total angular range of each of α1 (first outer circumference bevel surface angle data) and α2 (second outer circumference bevel surface angle data).

FIG. 23 A view showing the case when hypothesizing the value at each angular position θ of each of α1 (first outer circumference bevel surface angle data) and α2 (second outer circumference bevel surface angle data) to be an average values of first approximation values.

FIG. 24A A view expressing the first approximation value at each angular position θ of each of B1 (first outer circumference bevel surface axial direction component length data) and B2 (second outer circumference bevel surface axial direction component length data).

FIG. 24B A view expressing a maximum value (MAX), minimum value (MIN), average value (AVE), and standard deviation (STD) of a first approximation value at the total angular range of each of B1 (first outer circumference bevel surface axial direction component length data) and B2 (second outer circumference bevel surface axial direction component length data).

FIG. 25A A view expressing a second approximation value at each angular position θ of each of A1 (first outer circumference bevel surface diametrical direction component length data) and A2 (second outer circumference bevel surface diametrical direction component length data).

FIG. 25B A view expressing a maximum value (MAX), minimum value (MIN), average value (AVE), and standard deviation (STD) of a second approximation value at the total angular range of each of A1 (first outer circumference bevel surface diametrical direction component length data) and A2 (second outer circumference bevel surface diametrical direction component length data).

FIG. 26 A view of the case when hypothesizing the value at each angular position θ of each of A1 (first outer circumference bevel surface diametrical direction component length data) and A2 (second outer circumference bevel surface diametrical direction component length data) to be an average value of the second approximation values.

FIG. 27A A view expressing a second approximation value at each angular position θ of each of B1 (first outer circumference bevel surface axial direction component length data) and B2 (second outer circumference bevel surface axial direction component length data).

FIG. 27B A view expressing a maximum value (MAX), minimum value (MIN), average value (AVE), and standard deviation (STD) of a second approximation value at the total angular range of each of B1 (first outer circumference bevel surface axial direction component length data) and B2 (second outer circumference bevel surface axial direction component length data).

FIG. 28A A view expressing a second approximation value at each angular position θ of each of α1 (first outer circumference bevel surface angle data) and α2 (second outer circumference bevel surface angle data).

FIG. 28B A view expressing a maximum value (MAX), minimum value (MIN), average value (AVE), and standard deviation (STD) of a second approximation value at the total angular range of each of α1 (first outer circumference bevel surface angle data) and α2 (second outer circumference bevel surface angle data).

FIG. 29A A view expressing a value at an angular position θ corresponding to a thickness T of a semiconductor wafer in the case when hypothesizing that the value at each angular position θ of each of B1 (first outer circumference bevel surface axial direction component length data) and B2 (second outer circumference bevel surface axial direction component length data) is an n-th approximation value.

FIG. 29B A view expressing a maximum value (MAX), minimum value (MIN), average value (AVE), and standard deviation (STD) of a second approximation value in the total angular range of a thickness T of the semiconductor wafer when hypothesizing that the value at each angular position θ of each of B1 (first outer circumference bevel surface axial direction component length data) and B2 (second outer circumference bevel surface axial direction component length data) is an n-th approximation value.

REFERENCE SIGNS LIST

10 CCD camera
10a first CCD camera
10b second CCD camera
10c third CCD camera
11 camera lens
12 camera body
20 processing unit
31 first mirror
32 second mirror
33 correction lens
40 display unit
50 rotation drive motor
51 turntable
100 semiconductor wafer
101 outer circumference edge part
101a outer circumference end face
101b first outer circumference bevel surface
101c second outer circumference bevel surface
102 notch

DESCRIPTION OF EMBODIMENTS

Below, embodiments of the present invention will be explained using the drawings.

A silicon semiconductor wafer to be inspected by an edge inspection apparatus according to an embodiment of the present invention is structured as shown in FIG. 1A and FIG. 1B. Note that, FIG. 1A is a perspective view of a semiconductor wafer, while FIG. 1B is a cross-sectional view along the line A-A of FIG. 1A. As shown in FIG. 1A and FIG. 1B, an outer circumference edge part 101 of a disk-shaped semiconductor wafer 100 is comprised of an outer circumference end face 101a of the semiconductor wafer 100, a first outer circumference bevel surface 101b slanted at an outer circumference rim of one surface of the semiconductor wafer 100 (first surface), and a second outer circumference bevel surface 101c slanted at an outer circumference rim of another surface of the semiconductor wafer 100. At that outer circumference edge part 101, a notch 102 is formed expressing a reference position in the circumferential direction (Ds).

The basic configuration of the imaging system in an edge inspection apparatus according to an embodiment of the present invention becomes as shown in FIG. 2. Note that, the configuration of the mechanical system of this edge inspection apparatus as a whole may, for example, be made similar to that described in the Patent Literature 2.

In FIG. 2, the semiconductor wafer 100 configured as explained above (see FIG. 1A and FIG. 1B) is, for example, set on a turntable (not shown in FIG. 2) and can turn together with that turntable about its rotational shaft Lc. Facing the outer circumference edge part 101 of the semiconductor wafer 100 set on the turntable, an imaging unit comprised of three CCD cameras, that is, a first CCD camera 10a, second C=D camera 10b, and third CCD camera 10c, is set. The first CCD camera 10a faces the outer circumference end face 101a of the semiconductor wafer 100. A CCD line sensor 11a inside it is set to an orientation so as to extend in a direction (Da) cutting across the outer circumference end face 101a substantially perpendicularly to its circumferential direction (Ds: direction vertical to paper surface of FIG. 2). The second CCD camera 10b faces the first outer circumference bevel surface 101b of the semiconductor wafer 100. A CCD line sensor 11b inside it is set to an orientation so as to extend in a direction (Db) cutting across the first outer circumference bevel surface 101b substantially perpendicularly to its circumferential direction (Ds). The third CCD camera 10c faces the second outer circumference bevel surface 101c of the semiconductor wafer 100. A CCD line sensor 11c inside it is set to an orientation so as to extend in a direction (Dc) cutting across the second outer circumference bevel surface 101c substantially perpendicularly to its circumferential direction (Ds).

In the process of the semiconductor wafer 100 turning, the CCD line sensor 11a of the first CCD camera 10a successively scans that outer circumference end face 101a in the circumferential direction (Ds) (sub scan). Due to this, the first CCD camera 10a successively captures the outer circumference end face 101a in the circumferential direction (Ds) and outputs an image signal in pixel units. Further, in that process, the CCD line sensor 11b of the second CCD camera 10b successively scans the first outer circumference bevel surface 101b of the semiconductor wafer 100 in the circumferential direction (Ds) (sub scan) and the CCD line sensor 11c of the third CCD camera 10c successively scans the second outer circumference bevel surface 101c in the circumferential direction (Ds) (sub scan). Due to this, the second CCD camera 10b captures the first outer circumference bevel surface 101b and the third CCD camera 10c captures the second outer circumference bevel surface 101c in the circumferential direction (Ds) and output image signals in pixel units.

A control system of an edge inspection apparatus according to an embodiment of the present invention is configured as shown in FIG. 3.

In FIG. 3, the first CCD camera 10a, second CCD camera 10b, and third CCD camera 10c are connected to a processing unit 20 formed by a computer. The processing unit 20 controls the drive of a rotation drive motor 50 so as to turn a turntable 51 on which a semiconductor wafer 100 is set in a horizontal state by an alignment mechanism at a predetermined speed and processes image signals successively output from the first CCD camera 10a, second CCD camera 10b, and third CCD camera 10c. Further, the processing unit 20 is connected to a display unit 40. The processing unit 20 displays images based on image information generated from the image signals, information expressing inspection results obtained by processing the image information, etc. on the display unit 40.

Note that, the imaging unit capturing the outer circumference edge part 101 of the semiconductor wafer 100 need not be configured by three CCD cameras 10a, 10b, and 10c. For example, as shown in FIG. 4, it may also be configured by a single CCD camera 10. In this case, near the first outer circumference bevel surface 101b at the outer circumference edge part 101 of the semiconductor wafer 100, a first mirror 31 is set, while near the second outer circumference bevel surface 101c, a second mirror 32 is set. The slants of the first mirror 31 and second mirror 32 are set so that the direction in which the image of the first outer circumference bevel surface 101b reflected at the first mirror 31 is led and the direction in which the image of the second outer circumference bevel surface 101c reflected at the second mirror 32 is led become parallel.

The CCD camera 10 has a camera lens 11 and a camera body 12. The camera body 12 is provided with a CCD line sensor and is designed so that an image led through the camera lens 11 is formed on that CCD line sensor. The cm camera 10 has a visual field including the outer circumference edge part 101 of the semiconductor wafer 100 and is arranged at a position where the image of the first outer circumference bevel surface 101b and the image of the second outer circumference bevel surface 101c led through the first mirror 31 and second mirror 32 are focused on the imaging surface of the CCD line sensor.

The image of the outer circumference end face 101a of the semiconductor wafer 100 passes through the camera lens 11 of the CCD camera 10 and is formed on the imaging surface of the CCD line sensor in the camera body 12. In this case, the optical path length from the first outer circumference bevel surface 101b (second outer circumference bevel surface 101c) through the first mirror 31 (second mirror 32) to the camera unit 10 and the optical path length from the outer circumference end face 101a to the camera unit 10 differ, so as that is, the image of the outer circumference end face 101a will not be focused on the imaging surface of the camera body 12. Therefore, between the outer circumference end face 101a of the semiconductor wafer 100 and the CCD camera 10, a correction lens 33 is set. This correction lens 33 and camera lens 11 are used to guide the image of the outer circumference end face 101a of the semiconductor wafer 100 so as to be focused on the imaging surface of the CCD line sensor in the camera body 12.

In this way, the optical system arranged between the CCD camera 10 and the outer circumference edge part 101 of the semiconductor wafer 100 (first mirror 31, second mirror 32, and correction lens 33) is used so that the images of the outer circumference end face 101a, first outer circumference bevel surface 101b, and second outer circumference bevel surface 101c of the outer circumference edge part 101 are focused on the imaging surface of the CCD line sensor of the CCD camera 10. Due to this, the image signals successively output from the CCD camera 10 express the different parts of the outer circumference end face 101a, first outer circumference bevel surface 101b, and second outer circumference bevel surface 101c.

The processing unit 20 executes processing in accordance with the routine shown in FIG. 5 and FIG. 6.

In FIG. 5, the processing unit 20 makes the turntable 51 on which the semiconductor wafer 100 is set turn by a predetermined speed (S1). In the process of the semiconductor wafer 100 turning, the processing unit 20 receives as input image signals successively output from the first CCD camera 10a, second CCD camera 10b, and third CCD camera 10c, generates image information expressing the outer circumference edge part 101 of the semiconductor wafer 100 from these image signals (for example, shading data represented in predetermined gradation for each pixel), and stores that image information (image data) in a predetermined memory (not shown) (S2). Specifically, from the image signal from the first CCD camera 10a, as shown in FIG. 7, image data $I_{Ap}(\theta)$ expressing the outer circumference end face 101a of the semiconductor wafer 100 at each angular position $\theta$ in the circumferential direction (Ds) from the notch 102 ($\theta=0°$) (for example, by an angular resolution corresponding to the width of the CCD line sensor 11a) is generated, from the image signal from the second CCD camera 10b, image data $I_{Ub}(\theta)$ expressing the first outer circumference bevel surface 101b of the semiconductor wafer 100 at each angular position $\theta$ is generated, from the image signal from the third CCD camera 10c, image data $I_{Lb}(\theta)$ expressing the second outer circumference bevel surface 101c of the semiconductor wafer 100 at each angular position $\theta$ is generated, and these image data $I_{Ap}(\theta)$, $I_{Ub}(\theta)$, and $I_{Lb}(\theta)$ are stored in the memory in a state linked with the angular position $\theta$.

The processing unit 20, in the process of the processing, judges if one turn's worth of image data of the semiconductor wafer 100 has finished being fetched (stored in the memory) (S3). When one turn's worth of image data of the semiconductor wafer 100 has finished being fetched (YES at S3), the processing unit 20 stops the turning of the turntable 51 on which the semiconductor wafer 100 is set (S4). After this, it performs processing for image display based on the fetched image data $I_{Ap}(\theta)$, $I_{Ub}(\theta)$, and $I_{Lb}(\theta)$ (S5) and ends the series of processing.

Note that, when using a single CCD camera 10 as shown in FIG. 4, the processing unit 20 cuts out from the image signals from the CCD camera 10 the signal part corresponding to the outer circumference end face 101a, the signal part corresponding to the first outer circumference bevel surface 101b, and the signal part corresponding to the second outer circumference bevel surface 101c to generate from the signal parts the image data $I_{Ap}(\theta)$, $I_{Ub}(\theta)$, and $I_{Lb}(\theta)$ expressing the outer circumference end face 101a, first outer circumference bevel surface 101b, and second outer circumference bevel surface 101c.

Due to the processing for image display (S5), based on the image data $I_{Ub}(\theta)$ expressing the first outer circumference bevel surface 101b of one turn of the semiconductor wafer 100, for example, as shown in FIG. 8(a), the image I(Ub) of the first outer circumference bevel surface 101b in the visual field Eb of the second CCD camera 10b is displayed on the display unit 40. Further, based on the image data $I_{Ap}(\theta)$ expressing the outer circumference end face 101a of one turn of the semiconductor wafer 100, for example, as shown in FIG. 9(a), the image I(Ap) of the outer circumference end face 101a in the visual field Ea of the first CCD camera 10a is displayed on the display unit 40, furthermore, based on the image data $I_{Lb}(\theta)$ expressing the second outer circumference bevel surface 101c of one turn of the semiconductor wafer 100, for example, as shown in FIG. 10(a), the image I(Lb) of the second outer circumference bevel surface in the visual field Ec of the third CCD camera 10c is displayed on the display unit 40.

Note that, display unit 40 can be made to display the screen by scrolling in a case where all of the images of one turn of the semiconductor wafer for the first outer circumference bevel surface 101b, outer circumference end face 101a, and second outer circumference bevel surface 101c cannot be displayed all together.

As shown in FIG. 8(a), FIG. 9(a), and FIG. 10(a), the images I(Ub), I(AP), and I(Lb) of the first outer circumference bevel surface 101b, outer circumference end face 101a, and second outer circumference bevel surface 101c displayed on the display unit 40 can express cracks, particles, or other defects d2, d1, and d3. By observing the images displayed on such a display unit 40, it is possible to inspect at what positions of the outer circumference edge part 101 of the semiconductor wafer 100 (first outer circumference bevel surface 101b, outer circumference end face 101a, and second outer circumference bevel surface 101c) (angular position θ from the notch 102) there are defects.

The processing unit 20 responds to a predetermined operation at the operation unit (not shown) and performs processing relating to shape inspection of the outer circumference edge part 101 of the semiconductor wafer 100 in accordance with the routine shown in FIG. 6.

In FIG. 6, the processing unit 20 sets the angular position θ at an initial value (for example, θ=0°) (S11) and reads out three types of image data $I_{AP}(θ)$, $I_{Ub}(θ)$, and $I_{Lb}(θ)$ (S12) stored in the memory as explained above in response to this angular position θ. Further, the processing unit 20 generates edge shape information expressing the shape of the first outer circumference bevel surface 101b at the angular position θ based on image data $I_{Ub}(θ)$ expressing the first outer circumference bevel surface 101b (S13). Specifically, as shown in FIG. 8, based on the state of change (change of shading) of the image data $I_{Ub}(θ)$ at the angular position θ (see FIG. 8(b)), the boundaries of the image I(Ub) of the first outer circumference bevel surface 101b are detected and the first outer circumference bevel surface length data Ub(θ) expressed by the number of pixels between the image boundaries (or converted to distance by the pitch of pixels of the CCD line sensor 11b) is generated as edge shape information. This first outer circumference bevel surface length data Ub(θ) expresses the length in a direction cutting across the circumferential direction (Ds) at the angular position θ of the first outer circumference bevel surface 101b approximately perpendicularly (see FIG. 8(a)).

The processing unit 20 similarly generates edge shape information expressing the outer circumference end face 101a and edge shape information expressing the shape of the second outer circumference bevel surface 101c (S13). Specifically, as shown in FIG. 9, based on the state of change of the image data $I_{AP}(θ)$ at the angular position θ (change of shading) (see FIG. 9(b)), the boundaries of the image I(Ap) of the outer circumference end face 101a are detected and the outer circumference end face length data Ap(θ) expressed by the number of pixels between the image boundaries is generated as edge shape information. This outer circumference end face length data Ap(θ) expresses a length in a direction cutting across the circumferential direction (DS) of the outer circumference end face 101a at the angular position θ approximately perpendicularly (see FIG. 9(a)). Further, for the shape of the second outer circumference bevel surface 101c, as shown in FIG. 10, based on the state of change (change of shading) of the image data $I_{Lb}(θ)$ at the angular position θ (see FIG. 10(b)), the boundaries of the image I(Lb) of the second outer circumference bevel surface 101c are detected and second outer circumference bevel surface length data Lb(θ) expressed by the number of pixels between the image boundaries is generated as the edge shape information. This second outer circumference bevel surface length data Lb(θ) expresses the length of a direction cutting across the circumferential direction (Ds) at the angular position θ of the second outer circumference bevel surface 101c approximately perpendicularly (see FIG. 10(a)).

Returning to FIG. 6, the processing unit 20 stores the first outer circumference bevel surface length data Ub(θ), outer circumference end face length data Ap(θ), and second outer circumference bevel surface length data Lb(θ) as edge shape information of the angular position θ generated in the above way in a predetermined memory linked with the angular position θ (S14). After this, the processing unit 20 judges if the angular position θ has reached 360° (θ=360°) (S15). If the angular position θ does not reach 360° (NO at S15), it judges that the processing for one turn of the semiconductor wafer 100 is not ended and increases the angular position θ by exactly the amount of a predetermined angle Δθ (θ=θ+Δθ: S16). Further, the processing unit 20 performs similarly processing again as the above-mentioned processing for that new angular position θ (S12 to S16). Due to this, the first outer circumference bevel surface length data Ub(θ), outer circumference end face length data Ap(θ), and second outer circumference bevel surface length data Lb(θ) at the new angular position θ are stored in a predetermined memory linked with that angular position θ (S14).

When it is judged that the angular position θ has reached 360° (YES at S15), it is judged that the processing of one turn of the semiconductor wafer 100 has ended. The processing unit 20 executes output processing (S17) and ends the series of processing.

By the above output processing, for example, graphs where the first outer circumference bevel surface length data Ub(θ), outer circumference end face length data Ap(θ), and second outer circumference bevel surface length data Lb(θ) generated as explained above are plotted corresponding to a plurality of angular positions θ are displayed as inspection results on the display unit 40. For a certain semiconductor wafer 100, a graph where the first outer circumference bevel surface length data Ub(θ) is plotted so as to correspond to the angular position θ is displayed as the broken line Q11 (solid line) or the broken line Q21 (dotted line) of FIG. 11, a graph where the outer circumference end face length data Ap(θ) is plotted so as to correspond to the angular position θ is displayed as the broken line Q12 (solid line) or the broken line Q22 (dotted line) of FIG. 12, and, further, a graph where the second outer circumference bevel surface length data Lb(θ) is plotted to correspond to the angular position θ is displayed as the broken line Q13 (solid line) or the broken line Q23 (dotted line) of FIG. 13. For example, from the broken lines Q11, Q12, and Q13, at the semiconductor wafer 100 being inspected, the outer circumference end face length Ap (see broken line Q12) is stable over the entire circumference, but it is learned that the first outer circumference bevel surface length Ub (see broken line Q11) and second outer circumference bevel surface length Lb (broken line Q13) fluctuate relatively largely at the angular position range θ=90° to 180°. From this, the semiconductor wafer 100 being inspected can be evaluated as changing in shape relatively largely at the first outer circumference bevel surface 101b and second outer circumference bevel surface 101c at the angular position range 90° to 180° compared with other angular position ranges. This evaluation result can be utilized as useful information in the next processing step such as processing for forming a film on the semiconductor wafer 100. Further, in the previous processing step for forming the outer circumference edge part 101 of the semiconductor wafer 100 (outer circumference end face 101a, first outer circumference bevel surface 101b, and second outer circumference bevel surface 101c) as well, the evaluation result can be utilized as useful information.

Note that, the outer circumference end face length data Ap(θ), first outer circumference bevel surface length data Ub(θ), and second outer circumference bevel surface length data Lb(θ) at each angular position θ may, as shown in FIG. 14A, be graphed all together for output as inspection results. Further, the maximum value (MAX), minimum value (MIN), average value (AVE), and standard deviation (STD) of each of Ap, Ub, and Lb at the total angular position range (0° to 360°) may, for example, as shown in FIG. 14B, be tabularized for output as inspection results.

When graphing all together the outer circumference end face length data Ap(θ), first outer circumference bevel surface length data Ub(θ), and second outer circumference bevel surface length data Lb(θ) corresponding to each angular position θ for display (output) as the inspection results, it becomes possible to visually judge the shape of the outer circumference edge part (outer circumference end face 101a, first outer circumference bevel surface 101b, and second outer circumference bevel surface 101c) of the semiconductor wafer 100 based on the shape of the graph. Further, when tabularizing the maximum value (MAX), minimum value (MIN), average value (AVE), and standard deviation (STD) of each of the Ap, Ub, and Lb at the total angular position range (0° to 360°) for display (output) as inspection results, in the production process of a semiconductor wafer 100, it becomes possible to easily manage the trends in the shape of the outer circumference edge part of a semiconductor wafer 100 based on the trends in these statistical values.

Note that, for example, as shown in FIG. 15A and FIG. 15B, even when the cross-sectional shape of the outer circumference edge part 101 is curved, image data corresponding to the outer circumference end face 101a, first outer circumference bevel surface 101a, and second outer circumference bevel surface 101c as shown by the dotted line is obtained. Therefore, even when the cross-sectional shape of the outer circumference edge part 101 is curved in this way, in the same way as explained above, the first outer circumference bevel surface length data Ub(θ), outer circumference end face length data Ap(θ), and second outer circumference bevel surface length data Lb(θ) at the plurality of angular positions θ can be used to evaluate the external shape of the outer circumference edge part 101 of the semiconductor wafer 100.

The edge inspection apparatus such as explained above is particularly effective for determining the trends in the overall shape of the outer circumference edge part 101 for each semiconductor wafer 100 (individual specimen).

As explained above, the image data $I_{Ap}(θ)$, $I_{Ub}(θ)$, and $I_{Lb}(θ)$ generated from the image signals output from the first CCD camera 10a, second CCD camera 10c, and third CCD camera 10b capturing the outer circumference edge part 101 of the semiconductor wafer 100 can express cracks, particles, or other defects dl, d2, and d3 of the outer circumference end face 101a, first outer circumference bevel surface 101b, and second outer circumference bevel surface 101c at the outer circumference edge part 101. Therefore, in the edge inspection apparatus, from that type of image data $I_{AP}(θ)$, $I_{Ub}(θ)$, and $I_{Lb}(θ)$, as the edge shape information expressing the shape of the outer circumference edge part 101, the outer circumference end face length data Ap(θ) expressing the shape of the outer circumference end face 101a, the first outer circumference bevel surface length data Ub(θ) expressing the shape of the first outer circumference bevel surface 101b, and the second outer circumference bevel surface length data Lb(θ) expressing the shape of the second outer circumference bevel surface 101c are generated, so it becomes possible to easily inspect the shape of the outer circumference edge part 101 by the same process or same apparatus as the inspection for the presence of cracks, particles, or other defects dl, d2, and d3 at the outer circumference edge part 101 based on the image data $I_{AP}(θ)$, $I_{Ub}(θ)$, and $I_{Lb}(θ)$ (see FIG. 8, FIG. 9, and FIG. 10).

In the above-mentioned example, as the edge shape information expressing the shape of the outer circumference edge part 101 of the semiconductor wafer 100, outer circumference end face length data Ap(θ) expressing a length in a direction cutting across the circumferential direction at a plurality of angular positions θ of the outer circumference end face 101a approximately perpendicularly, first outer circumference bevel surface length data Ub(θ) expressing a length of a direction cutting across the circumferential direction at a plurality of angular positions θ of the first outer circumference bevel surface 101b approximately perpendicularly, and second outer circumference bevel surface length data Lb(θ) expressing the length in a direction cutting across the circumferential direction at a plurality of angular positions θ of the second outer circumference bevel surface 101c approximately perpendicularly were used, but that edge shape information may also be one or more of these or may be other information. For example, as shown in FIG. 16, at least one of first outer circumference bevel surface angle data α1 expressing a slant angle at each of a plurality of angular positions θ of the first outer circumference bevel surface 101b, second outer circumference bevel surface angle data α2 expressing a slant angle at each of a plurality of angular positions θ of the second outer circumference bevel surface 101c, first outer circumference bevel surface diametrical direction component length data A1 expressing a length component in the diametrical direction of the semiconductor wafer 100 at each of a plurality of angular positions θ of the first outer circumference bevel surface 101b, second outer circumference bevel surface diametrical direction component length data A2 expressing a length component in the diametrical direction at each of a plurality of angular positions θ of the second outer circumference bevel surface 101c, first outer circumference bevel surface axial direction component length data B1 expressing a length component in the axial direction vertical to the semiconductor wafer 100 at each of a plurality of angular positions θ of the first outer circumference bevel surface 101b, and second outer circumference bevel surface axial direction component length data B2 expressing a length component in the axial direction at each of a plurality of angular positions θ of the second outer circumference bevel surface 101c may be generated as the edge shape information.

The first outer circumference bevel surface angle data α1, second outer circumference bevel surface angle data α2, first outer circumference bevel surface diametrical direction component length data A1, second outer circumference bevel surface diametrical direction component length data A2, first outer circumference bevel surface axial direction component length data B1, and second outer circumference bevel surface axial direction component length data B2, as explained above, may be calculated in accordance with various techniques from the outer circumference surface length data Ap(θ), first outer circumference bevel surface length data Ub(θ), and second outer circumference bevel surface length data Lb(θ) generated from the image data $I_{AP}(θ)$ $I_{Ub}(θ)$, and $I_{Lb}(θ)$ (see FIG. 16).

For example, in FIG. 16, $$Ub = A1/\cos \alpha 1 \quad (1)$$

$$B1 = Ub \cdot \sin \alpha 1 \quad (2)$$

where, $$B1 = B2 = (T-Ap)/2 \quad (3)$$

is hypothesized. Note that, T is the thickness of the semiconductor wafer 100 (for example, T=755 μm).

As explained above, for each of a plurality of (for example, 10) semiconductor wafers 100 for which the Ap (outer circumference surface length data), Ub (first outer circumference bevel surface length data), and Lb (second outer circumference bevel surface length data) have already been generated from the image data, first outer circumference bevel surface axial direction component length data B1 (i) at a certain angular position θ is calculated in accordance with the equation (3) (i is a number identifying the semiconductor wafer 100, i=1, . . . 10).

Further, the average value B1ave of that B1(1), B1(2), . . . , B1(10) is calculated in accordance with $$B1\text{ave} = \{B1(1) + B1(2) + \ldots + B1(10)\}/10 \quad (4)$$

This average value B1ave is returned to the equation (2)

$$B1\text{ave} = Ub \cdot \sin \alpha 1,$$

so in accordance with $$\alpha 1 = \sin^{-1}(B1\text{ave}/Ub) \quad (5)$$

the first outer circumference bevel surface angle data α1 at a certain angular position θ is calculated.

Further, from the equation (1), the first outer circumference bevel surface diametrical direction component length data A1 at a certain angular position θ is calculated in accordance with:

$$A1 = Ub \cdot \cos \alpha 1$$

Note that, the second bevel surface axial direction component length B2ave, second outer circumference bevel surface angle data α2, and second outer circumference bevel surface diametrical direction component length data A2 may also be similarly calculated.

For example, when using the first outer circumference bevel surface angle data α1 and second outer circumference bevel surface angle data α2 as the edge shape information, as the inspection results, a graph where the first outer circumference bevel surface angle data α1(θ) is plotted to correspond to each angular position θ is displayed like the broken line Q14 (solid line) or broken line Q24 (dotted line) of FIG. 17, and a graph where the second outer circumference bevel surface angle data α2(θ) is plotted to correspond to each angular position θ is displayed like the broken line Q15 (solid line) or the broken line Q25 (dotted line) of FIG. 18. In this case, for example, from the broken line Q15 of FIG. 18, it is learned that the second outer circumference bevel surface angle data α2 is comparatively larger in the angular position range 90° to 180°. From this, the semiconductor wafer 100 being inspected can be evaluated as one which changes in shape relatively largely at a slant angle of the second outer circumference bevel surface 101c of the angular position range 90° to 180° compared with other angular position ranges.

Furthermore, for example, when the graph of the first outer circumference bevel surface angle data α1(θ) (similar for second outer circumference bevel surface data α2(θ) as well) plotted to correspond to each angular position θ becomes the broken line Q26 (solid line) of FIG. 19, the first outer circumference bevel surface angle α1 becomes approximately constant over the entire circumference of the angular position of 0 degree to 360 degrees, but when the same graph becomes the broken line Q16 (dotted line) of FIG. 19, the first outer circumference bevel surface angle α1 greatly falls in the range of the angular position of 90 degrees to 270 degrees. If the outer circumference edge part 101 of the semiconductor wafer 100 has fluctuating parts of the first outer circumference bevel surface angle α1 like shown by the broken line Q16, in the resist film coating process, it will become difficult to uniformly coat a resist film over the entire circumference of the outer circumference edge part 101 of the semiconductor wafer 100. Further, if the coated resist film becomes uneven in thickness, eventually that resist film is liable to partially peel off and cause dust or to crack. Therefore, operationally, for example, when the first outer circumference bevel surface angle data α1 becomes a characteristic like the broken line Q16, by adjusting the processing conditions in the previous processing step forming the outer circumference edge part 101 to characteristics so that the first outer circumference bevel surface angle data α1 becomes like the broken line Q26, it becomes possible to reduce the obstructing factors in the post treatment process (film-forming process).

Note that, in the process of production of a semiconductor wafer 100, it is possible to perform an operation similar to the operation based on the above-mentioned α1 and α2 based on the other edge shape information (outer circumference surface length data Ap(θ), first outer circumference bevel surface length data Ub(θ), and second outer circumference bevel surface length data Lb(θ): see FIG. 11 to FIG. 13).

Next, still another example of the output processing (S17) will be explained.

As explained above, in FIG. 16, the following relationships stand.

$$B1 = Ub \cdot \sin \alpha 1 \quad (6)$$

$$\alpha 1 = \sin^{-1}(B1/Ub) \quad (7)$$

$$B2 = Lb \cdot \sin \alpha 2 \quad (8)$$

$$\alpha 2 = \sin^{-1}(B2/Lb) \quad (9)$$

$$A1 = Ub \cdot \cos \alpha 1 \quad (10)$$

$$\alpha 1 = \cos^{-1}(A1/Ub) \quad (11)$$

$$A2 = Lb \cdot \cos \alpha 2 \quad (12)$$

$$\alpha 2 = \cos^{-1}(A2/Lb) \quad (13)$$

$$T = Ap + B1 + B2 \text{ (T is thickness of semiconductor wafer } \mathbf{100}) \quad (14)$$

From the above relationships, in accordance with the technique of recursive regression, the values of the parameters α1 (first outer circumference bevel surface angle data), α2 (second outer circumference bevel surface angle data), A1 (first outer circumference bevel surface diametrical direction component length data), A2 (second outer circumference bevel surface diametrical direction component length data), B1 (first outer circumference bevel surface axial direction component length data), and B2 (second outer circumference bevel surface axial direction component length data) can be found.

Specifically, first, if hypothesizing that at each angular position θ, B1=B2, from the equation (14), the following relationship stands:

$$B1=B2=(T-Ap)/2 \quad (15)$$

Further, by entering the prescribed value of the thickness T of the semiconductor wafer 100 (for example, 755 μm) and the value of the Ap (outer circumference end face length data) at each angular position θ obtained as explained above into equation (15), the values of B1 and B2 (=B1) at each angular position θ are found as initial approximation values. Note that, the initial approximation values of B1 and B2 based on the above hypothesis, for example, as shown in FIG. 20, change in accordance with the change of the value of Ap (outer circumference end face length data) for each angular position θ.

The initial approximation value of B1 at each angular position θ and the Ub (first outer circumference bevel surface length data) at the corresponding angular position θ obtained as explained above are entered into equation (7) whereby the value of α1 at each angular position θ is obtained, while the initial approximation value of B2 (=B1) at each angular position θ and the Lb (second outer circumference bevel surface length data) at the corresponding angular position θ obtained as explained above are entered into equation (9) whereby the value of α2 at each angular position θ is found. Further, the value of α1 at each angular position θ and the Ub (first outer circumference bevel surface length data) at the corresponding angular position θ obtained as explained above are entered into equation (10) whereby the value of A1 at each angular position θ is found, while the value of α2 at each angular position θ and the Lb (second outer circumference bevel surface length data) at the corresponding angular position θ obtained as explained above are entered into equation (12) whereby the value of A2 at each angular position θ is found.

The approximation value of each of α1, α2, A1, and A2 at each angular position θ when hypothesizing that the values of B1 and B2 (=B2) at each angular position θ are the initial approximation values in this way is found as the first approximation value. After this, the maximum value (MAX), minimum value (MIN), average value (AVE), and standard deviation (STD) of the first approximation value of each of α1, α2, A1, and A2 at the total angular position range (0° to 360°) of the semiconductor wafer 100 being inspected are found. Note that, the first approximation value of each of A1 and A2 for each angular position θ calculated under the above hypothesis, for example, becomes as shown in FIG. 21A, while the maximum value (MAX), minimum value (MIN), average value (AVE), and standard deviation (STD) of each of A1 and A2 at the total angular position range (0° to 360°), for example, become as shown in FIG. 21B. Further, the first approximation value of each of α1 and α2 for each angular position θ calculated under the above hypothesis, for example, becomes as shown in FIG. 22A, while the maximum value (MAX), minimum value (MIN), average value (AVE), and standard deviation (STD) of each of α1 and α2 at the total angular position range (0° to 360°), for example, become as shown in FIG. 22B.

Next, it is hypothesized that the value of α1 at each angular position θ is the average value α1ave (fixed value) of the first approximation value and this average value α1ave and the Ub (first outer circumference bevel surface length data) at each angular position θ are entered into equation (6) whereby the value of B1 at each angular position θ is found, while it is hypothesized that the value of α2 at each angular position θ is the average value α2ave of the first approximation value and this average value α2ave and the Lb (second outer circumference bevel surface length data) at each angular position θ are entered into equation (8) whereby the value of B2 at each angular position θ is found. Further, the average value α1ave and the Ub (first outer circumference bevel surface length data) at each angular position θ are entered into equation (10) whereby the value of A1 at each angular position θ is found, while the average value α2ave of α2 and the Lb (second outer circumference bevel surface length data) of each angular position θ are entered into equation (12) whereby the value of A2 at each angular position θ is found.

The value of each of B1 and B2 at each angular position θ when hypothesizing that α1=α1ave and α2=α2ave at each angular position θ is found as a first approximation value, while the value of each of A1 and A2 at each angular position θ is found as a second approximation value. After this, the maximum values (MAX), minimum values (MIN), average values (AVE), and standard deviation values (STD) of the first approximation value of each of B1 and B2 and the second approximation value of each of A1 and A2 of the semiconductor wafer 100 being inspected at the total angular position (0° to 360°) are found. Note that, under the above hypothesis, the average values α1ave and α2ave of the first approximation values of α1 and α2 at each angular position θ are, for example, as shown in FIG. 23, constant, the first approximation value of each of B1 and B2 for each angular position θ calculated under that hypothesis, for example, becomes as shown in FIG. 24A, and the maximum value (MAX), minimum value (MIN), average value (AVE), and standard deviation (STD) of each of B1 and B2 at the total angular position range (0° to 360°), for example, become as shown in FIG. 24B. Further, the second approximation value of each of A1 and A2 for each angular position θ calculated under the above hypothesis, for example, becomes as shown in FIG. 25A, while the maximum value (MAX), minimum value (MIN), average value (AVE), and standard deviation (STD) of each of A1 and A2 at the total angular position range (0° to 360°), for example, become as shown in FIG. 25B.

Next, it is hypothesized that the value of A1 at each angular position θ is the average value A1ave (fixed value) of the second approximation value and this average value A1ave and the Ub (first outer circumference bevel surface length data) at each angular position θ are entered into equation (11) whereby the value of α1 at each angular position θ is found, while it is hypothesized that the value of A2 at each angular position θ is the average value A2ave (fixed value) of the second approximation value and this average value A2ave and the Lb (second outer circumference bevel surface length data) at each angular position θ are entered into equation (13) whereby the value of α2 at each angular position θ is found. Further, the value of α1 at each angular position θ and the Ub (first outer circumference bevel surface length data) at the corresponding angular position θ are entered into equation (6) whereby the value of B1 at each angular position θ is found, while the value of α2 at each angular position θ and the Lb (second outer circumference bevel surface length data) at the corresponding angular position θ are entered into equation (8) whereby the value of B2 at each angular position θ is found.

In this way, the value of each of α1 and α2 at each angular position θ is found as the second approximation value and the value of each of B1 and B2 at each angular position θ is found as the second approximation value when hypothesizing that A1=A1ave and A2=A2ave at each angular position θ. After this, the maximum value (MAX), minimum value (MIN), average value (AVE), and standard deviation value (STD) of the second approximation value of each of B1 and B2 and the second approximation value of each of α1 and α2 at the total angular position (0° to 360°) of the semiconductor wafer 100 being inspected are found. Note that, under the above hypothesis, the average values A1ave and A2ave of the second approximation values of A1 and A2 at each angular position θ are, for example, as shown in FIG. 26, constant, the second approximation value of each of B1 and B2 for each angular position θ calculated under that hypothesis, for example, becomes as shown in FIG. 27A, and the maximum value (MAX), minimum value (MIN), average value (AVE), and standard deviation (STD) of each of BE and B2 at the total angular position (0° to 360°), for example, become as shown in FIG. 27B. Further, the second approximation value of each of α1 and α2 for each angular position θ calculated under the above hypothesis, for example, becomes as shown in FIG. 28A, while the maximum value (MAX), minimum value (MIN), average value (AVE), and standard deviation (STD) of each of α1 and α2 at the total angular position range (0° to 360°), for example, become as shown in FIG. 28B.

After this, any of the set of the parameters B1 and B2, the set of the parameters A1 and A2, and the set of the parameters α1 and α2 is cyclically selected, the values at each angular position θ of the selected set of parameters is hypothesized as being the average values of the previously found approximation values, and the parameters of the other sets are computed based on this. This is successively repeated in the same way as explained above whereby the n-th approximation values at each angular position θ of each of the parameters B1, B2, A1, A2, α1, and α2 (technique of recursive regression) are found. Further, the n-th approximation values of the parameters B1, B2, and A1 obtained by repeating the above operations a predetermined number of times are output as the edge shape information.

The values (approximation values) of the edge shape information corresponding to each angular position θ may, for example, as shown in FIG. 21A, FIG. 22A, FIG. 24A, FIG. 25A, FIG. 27A, and FIG. 28A, be graphed for display (output) as the inspection results. Further, the statistical values of the maximum value (MAX), minimum value (MIN), average value (AVE), and standard deviation (STD) in the total angular range (0° to 360°) found from the values of the edge shape information at each angular position θ may, as shown in FIG. 21B, FIG. 22B, FIG. 24B, FIG. 25B, FIG. 27B, and FIG. 28B, be tabularized for display (output) as the inspection results. Note that the output format of the inspection results is not limited to the graph format and the table format and may be other formats as well.

When graphing the values (approximation values) of the edge shape information corresponding to the different angular positions θ of the semiconductor wafer 100 being inspected for display (output) as the inspection results, it becomes possible to visually judge the shape of the outer circumference edge part of the semiconductor wafer 100 based on the shape of the graph. Further, when tabularizing the statistical values of the maximum value (MAX), minimum value (MIN), average value (AVE), and standard deviation (STD) at the total angular range (0° to 360°) found from the values of the edge shape information of the semiconductor wafer 100 being inspected for display (output) as the inspection results, it is possible to easily manage the trends in the shape of the outer circumference edge part of a semiconductor wafer 100 based on the trends in these statistical values in the process of production of a semiconductor wafer 100.

In the above example, the statistical values (the maximum value (MAX), minimum value (MIN), average value (AVE), and standard deviation (STD) at the total angular range (0° to 360°)) of each of the parameters B1, B2, A1, A2, α1, and α2 were obtained for each of the semiconductor wafers 100, but the statistical values may also be obtained for each cassette in which a plurality of semiconductor wafers 100 are stored, for each lot of semiconductor wafers 100, or for each other unit. Further, the statistical values need not be all of the maximum value (MAX), minimum value (MIN), average value (AVE), and standard deviation (STD) and may be one or more of the same.

Note that, the value of each of the first outer circumference bevel surface axial direction component length data B1 and second outer circumference bevel surface axial direction component length B2 at each angular position θ obtained based on the above-mentioned technique of recursive regression and the values of the outer circumference end face length data Ap at the corresponding angular position θ obtained by measurement may be entered into the above-mentioned equation (14) to find the thickness T of the semiconductor wafer 100 at each angular position θ. The thickness T of the semiconductor wafer 100 at each angular range θ is found, for example, as shown in FIG. 29A, while further, the maximum value (MAX), minimum value (MIN), average value (AVE), and standard deviation (STD) of T are found, for example, as shown in FIG. 29B.

INDUSTRIAL APPLICABILITY

The edge inspection apparatus and edge inspection method of a semiconductor wafer according to the present invention has the advantageous effects of enabling easy inspection of the shape of outer circumference edge part of a semiconductor wafer by the same process or same apparatus as inspection for the presence of cracks, particles, or other defects at the outer circumference edge part and is useful as an edge inspection apparatus and edge inspection method of a semiconductor wafer for inspecting the outer circumference edge part of a semiconductor wafer.

The invention claimed is:

1. An edge inspection apparatus of a semiconductor wafer having:

an imaging unit arranged facing the outer circumference edge part of the semiconductor wafer, successively capturing the outer circumference edge part in a circumferential direction, and outputting an image signal;

an image processing unit processing the image signal successfully output from the imaging unit; and a display unit, the image processing unit having an image information generating means for generating image information expressing the outer circumference edge part of one turn of the semiconductor wafer from the image signal, a shape information generating means for generating edge shape information expressing shapes of a plurality of positions of the outer circumference edge part of one turn of the semiconductor wafer from the image information, an inspection result information generating means for generating inspection result information based on the edge shape information, the inspection result information being capable of expressing a state of the shape of the outer circumference edge part of one turn of the semiconductor wafer, first means for controlling the display unit based on the image information so that an image of the outer circumference edge part of the semiconductor wafer is displayed on the display unit, and second means for controlling the display unit based on the inspection result Information so that inspection result is displayed on the display unit.

2. The edge inspection apparatus of a semiconductor wafer as set forth in claim 1, wherein the imaging unit captures at least one of an outer circumference end face of the semiconductor wafer, a first outer circumference bevel surface slanted at an outer circumference rim of a first surface of the semiconductor wafer, and a second outer circumference bevel surface slanted at an outer circumference rim of a second surface at an opposite side from the first surface as the outer circumference edge part of the semiconductor wafer, and the shape information generating means generates at least one of information expressing the shape at each of a plurality of positions of the outer circumference end face from image information expressing an outer circumference end face of the semiconductor wafer, information expressing the shape at each of a plurality of positions of the first outer circumference bevel surface from image information expressing a first outer circumference bevel surface of the semiconductor wafer, and information expressing the shape at each of a plurality of positions of the second outer circumference bevel surface from image information expressing a second outer circumference bevel surface of the semiconductor wafer as the edge shape information.

3. The edge inspection apparatus of a semiconductor wafer as set forth in claim 2, wherein the shape information generating means generates at least one of outer circumference end face length information expressing a length in a direction cutting across the circumferential direction at each of a plurality of positions of the outer circumference end face from image information expressing the outer circumference end face, first outer circumference bevel surface length information expressing a length in a direction cutting across the circumferential direction at each of a plurality of positions of the first outer circumference bevel surface from image information expressing the first outer circumference bevel surface, and second outer circumference bevel surface length information expressing a length in a direction cutting across the circumferential direction at each of a plurality of positions of the second outer circumference bevel surface from image information expressing the second outer circumference bevel surface as the edge shape information.

4. The edge inspection apparatus of a semiconductor wafer as set forth in claim 2, wherein the shape information generating means generates outer circumference end face length information expressing a length in a direction cutting across the circumferential direction at each of a plurality of positions of the outer circumference end face from image information expressing the outer circumference end face, first outer circumference bevel surface length information expressing a length in a direction cutting across the circumferential direction at each of a plurality of positions of the first outer circumference bevel surface from image information expressing the first outer circumference bevel surface, and second outer circumference bevel surface length information expressing a length in a direction cutting across the circumferential directions at each of a plurality of positions of the second outer circumference bevel surface from image information expressing the second outer circumference bevel surface and, based on the outer circumference surface end face length information, the first outer circumference bevel surface length information, and the second outer circumference bevel surface length information, generates at least one of first outer circumference bevel surface angle information expressing a slant angle at each of said plurality of positions of the first outer circumference bevel surface, second outer circumference bevel surface angle information expressing a slant angle at each of said plurality of positions of the second outer circumference bevel surface, first outer circumference bevel surface diametrical direction component length information expressing a length component in a diametrical direction of the semiconductor wafer at each of the plurality of positions of the first outer circumference bevel surface, second outer circumference bevel surface diametrical direction component length information expressing a length component in the diametrical direction at each of the plurality of positions of the second outer circumference bevel surface, first outer circumference bevel surface axial direction component length information expressing a length component in an axial direct ion vertical to the semiconductor wafer at each of the plurality of positions of the first outer circumference bevel surface, and second outer circumference bevel surface axial direction component length information expressing a length component in the axial direction at each of the plurality of positions of the second outer circumference bevel surface as the edge shape information.

5. The edge inspection apparatus of a semiconductor wafer as set forth in claim 1, wherein the inspection result in formation generating means generates at least one of a maximum value, minimum value, average value, and standard deviation of a value of edge shape information at each of the plurality of positions based on edge shape information expressing a shape at each of a plurality of positions of the outer circumference edge part of one turn of the semiconductor wafer.

6. The edge inspection apparatus of a semiconductor wafer as set forth in claim 3, wherein the inspection result information generating means generates at least one of a maximum value, minimum value, average value, and standard deviation of a value of at least one of the outer circumference end face length information, the first outer circumference bevel surface length information, and the second outer circumference bevel surface length information at each of the plurality of positions of the outer circumference edge part of one turn of the semiconductor wafer.

7. The edge inspection apparatus of a semiconductor wafer as set forth in claim 4, wherein the inspection result information generating means generates at least one of a maximum value, minimum value, average value, and standard deviation of a value of at least one of first outer circumference bevel surface angle information, second outer circumference bevel surface angle information, first outer circumference bevel surface diametrical direction component length information, second outer circumference bevel surface diametrical direction component length information, first outer circumference bevel surface axial direction component length information, and second outer circumference bevel surface axial direction component length information at each of a plurality of positions of the outer circumference edge part of one turn of the semiconductor wafer.

8. An edge inspection method of a semiconductor wafer having an edge capturing step for using an imaging unit arranged facing an outer circumference edge part of a semiconductor wafer to capture an outer circumference edge part; and an image processing step for processing an image signal capturing the outer circumference edge part of the semiconductor wafer successively output from the imaging unit;

the image processing step having an image information generating step for generating image information expressing the outer circumference edge part of one turn of the semiconductor wafer from the image signal, a shape information generating step for generating edge shape information expressing a shape at each of a plurality of positions of the outer circumference edge part of one turn of the semiconductor wafer from the image information, an inspection result information generating step of generating inspection result information based on the edge shape Information, the inspection result information being capable of expressing a state of the shape of the outer circumference edge part of one turn of the semiconductor wafer, a step of controlling a display unit based on the image information so that an image of the outer circumference edge part of the semiconductor is displayed by the display unit, and a step of controlling the display unit based on the inspection result information so that inspection result is displayed by the display unit.

9. The edge inspection method of a semiconductor wafer as set forth in claim 8, wherein the edge capturing step uses the imaging unit to capture at least one of an outer circumference end face of the semiconductor wafer, a first outer circumference bevel surface slanted at an outer circumference rim of a first surface of the semiconductor wafer, and a second outer circumference bevel surface slanted at an outer circumference rim of a second surface at an opposite side from the first surface as the outer circumference edge part of the semiconductor wafer, and the shape information generating step generates at least one of information expressing a shape at each of a plurality of positions of the outer circumference end face from image information expressing an outer circumference end face of the semiconductor wafer, information expressing a shape at each of a plurality of positions of the first outer circumference bevel surface from image information expressing a first outer circumference bevel surface of the semiconductor wafer, and information expressing a shape at each of a plurality of positions of the second outer circumference bevel surface from image information expressing a second outer circumference bevel surface of the semiconductor wafer as the edge shape information.

10. The edge inspection method of a semiconductor wafer as set forth in claim 9, wherein the shape information generating step generates at least one of outer circumference end face length information expressing a length of a direction cutting across the circumferential direction at each of a plurality of positions of the outer circumference end face from image information expressing the outer circumference end face, first outer circumference bevel surface length information expressing a length in a direction cutting across the circumferential direction at each of a plurality of positions of the first outer circumference bevel surface from image information expressing the first outer circumference bevel surface, and second outer circumference bevel surface length information expressing a length in a direction cutting across the circumferential direction at each of a plurality of positions of the second outer circumference bevel surface from image information expressing the second outer circumference bevel surface as the edge shape information.

* * * * *